(12) United States Patent
Archibald et al.

(10) Patent No.: US 11,559,785 B2
(45) Date of Patent: *Jan. 24, 2023

(54) METHOD FOR SEPARATION OF RADIOACTIVE SAMPLE USING MONOLITHIC BODY ON MICROFLUIDIC CHIP

(71) Applicant: The University of Hull, Hull Humberside (GB)

(72) Inventors: Stephen James Archibald, Hull Humberside (GB); Ping He, Hull Humberside (GB); Stephen John Haswell, Hull Humberside (GB); Nicole Pamme, Hull Humberside (GB); Nathan Joel Brown, Hull Humberside (GB); Mark Duncan Tarn, Hull Humberside (GB); Richard Alexander, Hull Humberside (GB); Mohammad Mehdi Nasr Esfahani, Hull Humberside (GB)

(73) Assignee: The University of Hull, Hull Humberside (GB)

( * ) Notice: Subject to any disclaimer, the term of this patent is extended or adjusted under 35 U.S.C. 154(b) by 161 days.

This patent is subject to a terminal disclaimer.

(21) Appl. No.: 15/521,198

(22) PCT Filed: Oct. 22, 2015

(86) PCT No.: PCT/GB2015/053171
§ 371 (c)(1),
(2) Date: Apr. 21, 2017

(87) PCT Pub. No.: WO2016/063070
PCT Pub. Date: Apr. 28, 2016

(65) Prior Publication Data
US 2017/0368534 A1    Dec. 28, 2017

(30) Foreign Application Priority Data

Oct. 23, 2014 (GB) ..................... 1418893

(51) Int. Cl.
*G01N 33/15* (2006.01)
*G01N 30/02* (2006.01)
(Continued)

(52) U.S. Cl.
CPC ...... *B01J 20/28042* (2013.01); *B01D 15/322* (2013.01); *B01D 15/362* (2013.01);
(Continued)

(58) Field of Classification Search
CPC .............. B01J 20/28042; B01J 2220/82; B01J 2220/825; G01N 2033/0093;
(Continued)

(56) References Cited

U.S. PATENT DOCUMENTS

| | | |
|---|---|---|
| 5,757,482 A | 5/1998 | Fuchs et al. |
| 5,770,030 A | 6/1998 | Hamacher et al. |

(Continued)

FOREIGN PATENT DOCUMENTS

| | | |
|---|---|---|
| CN | 101035602 A | 9/2007 |
| CN | 101146609 B | 3/2008 |

(Continued)

OTHER PUBLICATIONS

Nakao, R. et al. "Improved radiometabolite analysis procedure for positron emission tomography (PET) radioligands using a monolithic column coupled with direct injection micellar/high submicellar liquid chromatography," Talanta 113 (2013) 130-134; available online Mar. 15, 2013. (Year: 2013).*

(Continued)

*Primary Examiner* — Jennifer Wecker
*Assistant Examiner* — Michelle Adams
(74) *Attorney, Agent, or Firm* — Sheridan Ross P.C.

(57) ABSTRACT

The present invention relates to monolithic bodies, uses thereof and processes for the preparation thereof. Certain embodiments of the present invention relate to the use of a monolithic body in the preparation of a radioactive substance, for example a radiopharmaceutical, as part of a microfluidic flow system and a process for the preparation of such a monolithic body.

20 Claims, 10 Drawing Sheets

(51) Int. Cl.
*B01J 20/28* (2006.01)
*B01J 39/26* (2006.01)
*B01J 41/20* (2006.01)
*B01J 20/283* (2006.01)
*B01J 19/00* (2006.01)
*G21G 1/00* (2006.01)
*B01J 20/291* (2006.01)
*B01L 3/00* (2006.01)
*B01D 15/32* (2006.01)
*B01D 15/36* (2006.01)
*B01J 20/02* (2006.01)
*B01J 20/10* (2006.01)
*B01J 20/22* (2006.01)
*B01J 20/282* (2006.01)
*B01J 20/30* (2006.01)
*B29C 45/14* (2006.01)
*B29C 71/02* (2006.01)
*G01N 30/96* (2006.01)
*G01N 33/00* (2006.01)
*B29K 105/00* (2006.01)
*B29K 709/00* (2006.01)

(52) U.S. Cl.
CPC ........ *B01D 15/363* (2013.01); *B01J 19/0093* (2013.01); *B01J 20/02* (2013.01); *B01J 20/103* (2013.01); *B01J 20/22* (2013.01); *B01J 20/282* (2013.01); *B01J 20/283* (2013.01); *B01J 20/28061* (2013.01); *B01J 20/28092* (2013.01); *B01J 20/291* (2013.01); *B01J 20/3007* (2013.01); *B01J 20/3078* (2013.01); *B01J 39/26* (2013.01); *B01J 41/20* (2013.01); *B01L 3/5027* (2013.01); *B29C 45/14* (2013.01); *B29C 71/02* (2013.01); *G01N 30/96* (2013.01); *G01N 33/15* (2013.01); *G21G 1/001* (2013.01); *B01J 2219/0079* (2013.01); *B01J 2219/0086* (2013.01); *B01J 2219/00792* (2013.01); *B01J 2219/00813* (2013.01); *B01J 2219/00824* (2013.01); *B01J 2219/00867* (2013.01); *B01J 2219/00869* (2013.01); *B01J 2219/00916* (2013.01); *B01J 2220/82* (2013.01); *B01L 2200/10* (2013.01); *B29C 2071/022* (2013.01); *B29K 2105/0058* (2013.01); *B29K 2709/00* (2013.01); *G01N 2033/0093* (2013.01)

(58) Field of Classification Search
CPC .... G01N 33/0055; G01N 33/60; C07B 59/00; C07B 59/001; C07B 59/002; C07B 59/004; C07B 59/005; B01L 3/5027; B01L 3/502707; B01L 3/502753; B01L 2200/10

See application file for complete search history.

(56) References Cited

U.S. PATENT DOCUMENTS

| | | | |
|---|---|---|---|
| 6,030,552 | A | 2/2000 | Ambras et al. |
| 6,207,098 | B1* | 3/2001 | Nakanishi ............... B01J 20/10 264/413 |
| 6,827,095 | B2 | 12/2004 | O'Connor et al. |
| 7,670,559 | B2 | 3/2010 | Chien et al. |
| 8,077,311 | B1 | 12/2011 | Byrne et al. |
| 11,075,019 | B2* | 7/2021 | Archibald ............... C07B 59/00 |
| 11,369,955 | B2* | 6/2022 | Archibald ............. G01N 33/94 |
| 2003/0230524 | A1* | 12/2003 | Soga ...................... B01J 20/283 210/198.2 |
| 2004/0174657 | A1 | 9/2004 | Andelman et al. |
| 2004/0258615 | A1 | 12/2004 | Buchanan et al. |
| 2005/0079409 | A1 | 4/2005 | Andelman et al. |
| 2005/0226776 | A1 | 10/2005 | Brady et al. |
| 2005/0232387 | A1 | 10/2005 | Padgett et al. |
| 2005/0232861 | A1 | 10/2005 | Buchanan et al. |
| 2006/0160209 | A1 | 7/2006 | Larson et al. |
| 2006/0228812 | A1 | 10/2006 | Higashino et al. |
| 2007/0138076 | A1 | 6/2007 | Daridon et al. |
| 2007/0166199 | A1 | 7/2007 | Zhou et al. |
| 2008/0064110 | A1 | 3/2008 | Elizarov et al. |
| 2008/0093300 | A1 | 4/2008 | Clarke et al. |
| 2008/0153155 | A1 | 6/2008 | Kato et al. |
| 2008/0224072 | A1 | 9/2008 | Sonnenhol et al. |
| 2009/0036668 | A1 | 2/2009 | Elizarov et al. |
| 2009/0079409 | A1 | 3/2009 | Chang |
| 2009/0095635 | A1 | 4/2009 | Elizarov et al. |
| 2010/0069600 | A1 | 3/2010 | Morelle et al. |
| 2010/0101943 | A1 | 4/2010 | Iwata et al. |
| 2010/0210458 | A1 | 8/2010 | Katsuhara et al. |
| 2011/0000279 | A1* | 1/2011 | Miyazaki ............... B01J 20/103 73/23.35 |
| 2011/0070160 | A1 | 3/2011 | Nutt et al. |
| 2011/0100840 | A1 | 5/2011 | Nakanishi et al. |
| 2011/0150714 | A1 | 6/2011 | Elizarov et al. |
| 2012/0142118 | A1 | 6/2012 | Brenna et al. |
| 2012/0301372 | A1 | 11/2012 | Watanabe et al. |
| 2013/0248366 | A1 | 9/2013 | Haswell et al. |
| 2013/0337493 | A1 | 12/2013 | Hansteen et al. |
| 2014/0030800 | A1 | 1/2014 | Moses et al. |
| 2014/0316130 | A1 | 10/2014 | Brady et al. |
| 2015/0152206 | A1 | 6/2015 | Keng et al. |
| 2018/0025801 | A1 | 1/2018 | Archibald et al. |
| 2018/0033510 | A1 | 2/2018 | Archibald et al. |
| 2018/0169654 | A1 | 6/2018 | Archibald et al. |

FOREIGN PATENT DOCUMENTS

| | | | |
|---|---|---|---|
| CN | 102245305 | B | 11/2011 |
| CN | 104039166 | A | 9/2014 |
| EP | 1933330 | A1 | 6/2008 |
| EP | 2650681 | | 10/2013 |
| JP | 2005-257543 | | 9/2005 |
| JP | 2010-190602 | | 9/2010 |
| WO | 2003078358 | A2 | 9/2003 |
| WO | 2004093652 | A2 | 11/2004 |
| WO | 2006071470 | A2 | 7/2006 |
| WO | WO 2007/122819 | | 11/2007 |
| WO | 2008001098 | A1 | 1/2008 |
| WO | 2008091694 | A9 | 11/2008 |
| WO | 2008157801 | A2 | 12/2008 |
| WO | 2009015048 | A2 | 1/2009 |
| WO | 2011006166 | A1 | 1/2011 |
| WO | 2012009666 | A2 | 1/2012 |
| WO | 2013012798 | A1 | 1/2013 |
| WO | 2013049577 | A1 | 4/2013 |
| WO | 2013054129 | A1 | 4/2013 |
| WO | 2013188446 | A1 | 12/2013 |
| WO | 2014009379 | A1 | 1/2014 |
| WO | 2015039170 | A1 | 3/2015 |
| WO | 2016063068 | A2 | 4/2016 |
| WO | 2016063069 | A1 | 4/2016 |
| WO | 2016063070 | A1 | 4/2016 |
| WO | 2016063072 | A1 | 4/2016 |

OTHER PUBLICATIONS

Tarn, M.D. et al. "Purification of 2-[18F]fluoro-2-deoxy-d-glucose by on-chip solid-phase extraction," Journal of Chromatography A, 1280 (2013) 117-121; available online Jan. 15, 2013. (Year: 2013).*

Phenomenex. "Onyx—Monolithic Silica HPLC Columns" brochure, 6 pages, 2013; downloaded from <https://phenomenex.blob.core.windows.net/documents/2791ff52-0585-4146-9c00-fbb700e390f0.pdf> on Oct. 24, 2019 (Year: 2013).*

Meyer, G.-J. et al. "The stability of 2-[18F]fluoro-deoxy-d-glucose towards epimerisation under alkaline conditions," Applied Radiation and Isotopes 51 (1999) 37-41 (Year: 1999).*

(56) References Cited

OTHER PUBLICATIONS

Arima, V. et al. "Radiochemistry on chip: towards dose-on-demand synthesis of PET radiopharmaceuticals," Lab Chip, 2013, 13, 2328; Mar. 25, 2013 (Year: 2013).*
Guiochon, G. "Monolithic columns in high-performance liquid chromatography," Journal of Chromatography A, 1168 (2007) 101-168 (Year: 2007).*
Siouffi, A.-M. "Silica gel-based monoliths prepared by the sol—gel method: facts and figures," Journal of Chromatography A, 1000 (2003) 801-818 (Year: 2003).*
Cabrera, K. "Applications of silica-based monolithic HPLC columns," J. Sep. Sci. 2004, 27, 843-852 (Year: 2004).*
Alexoff et al. Recovery of [18F] Flouride From [18O] Water in an Electrochemical Cell Appl. Radiat. Isot. vol. 40 No. 1, pp. 1-6, 1989; Int. J. Radiat. Appl. Instrum Part 4.
Bruchet et al. Centrifugal Microfluidic Platform for Radiochemistry: Potentialities for the Chemical Analysis of Nuclear Spent Fuels; Talanta 116 (2013) pp. 488-494.
Elizarov et al. Design and Optimization of Coin-Shaped Microreactor Chips for PET Radiopharmaceutical Synthesis; Journal of Nuclear Medicine (2010) pp. 282-287.
Hamacher et al. Electrochemical Cell for Separation of [18F] Flouride From Irradiated 18O-Water and Subsequent No Carrier Added Nucleophilic Fluorinaton; Applied Radiation and Isotopes 56 (2002) pp. 519-523.
Hamacher et al. No-Carrier-Added Nucleophilic 18F-Labelling in an Electrochemical Cell Exemplified By the Routine Prodcution of [18F] Altanserin; Applied Radiation and Isotopes 64 (2006) pp. 989-994.
International Preliminary Report on Paentability issued in PCT/GB2015/053171, dated Apr. 25, 2017, 6 pages.
International Preliminary Report on Patentability issued for PCT/GB2015/053170, dated Apr. 25, 2017, 6 pages.
International Preliminary Report on Patentability issued for PCT/GB2015/053173, dated Apr. 25, 2017, 5 pages.
International Preliminary Report on Patentability issued in PCT/GB2015/053167, report dated Apr. 25, 2017, 17 pages.
International Search Report and Written Opinion issued in PCT/GB2015/053167, dated May 23, 2016, 26 pages.
International Search Report and Written Opinion issued in PCT/GB2015/053170, dated Feb. 4, 2016. 11 pages.
International Search Report and Written Opinion issued in PCT/GB2015/053173, dated Feb. 2, 2016, 10 pages.
Ismail et al. Cationic Imidazolium Polymer Monoliths for Efficient Solvent Exchange, Activation and Fluorinaton On a Continuous Flow System; RSC Adv. (2014), 4, 25348-25356.
Saiki, H. et al. Electrochemical Concentration of No-Carrier-Added [18F] Flouride From [18O] Water in a Disposable Microfluidic Cell for Radiosynthesis of 18F-Labeled Radiopharmaceuticals; Applied Radiation and Isotopes 68 (2010) pp. 1703-1708.
UK Search Report Issued in Application No. GB1418893.2, dated Nov. 3, 2015, 5 pages.
UK Search Report Issued in Application No. GB1418895.7, dated Apr. 24, 2015, 5 pages.
UK Search Report Issued in Application No. GB1418897.3, dated Jul. 10, 2015, 6 pages.
UK Search Report issued in Application No. GB1418899.9, dated Apr. 24, 2015, 4 pages.
Fletcher, Paul D. I., et al. Permeability of silica monoliths containing micro- and nano-pores. J Porous Mater, 18:501-508, 2011.
Li, Z. and Conti, P.S. Radiopharmaceutical chemistry for positron emission tomography. Advanced Drug Delivery Reviews, 62:1031-1051, 2010.
Mewis, R.E. and Archibald, S.J. (2010). Biomedical applications of macrocyclic ligand complexes. Coordination Chemistry Reviews, Review, 254:1686-1712.
Phelps, M.E. (2000). Positron emission tomography provides molecular imaging of biological processes. PNAS, 97 (16):9226-9233.
Silversides, J. D., Smith, R., Archibald, S. J. Challenges in chelating positron emitting copper isotopes: Tailored synthesis of unsymmetric chelators to form ultra stable complexes. Dalton Transactions, "Radiopharmaceuticals for Imaging and Therapy," 40:6289-6297, 2011.
Wood, Laura D., et al. The Genomic Landscapes of Human Breast and Colorectal Cancers. Sciencexpress, Research Article, Oct. 11, 2007, pp. 1-8 paginated and accompanying images.
Haroun, S.; et al. (2013). Continuous-flow synthesis of [11C]raclopride, a positron emission tomography radiotracer, on a microfluidic chip. Can. J. Chem. 91:326-332.
Grinias, J. et al. (2016) Advances in and prospects of microchip liquid chromatography. Trends in Analytical Chemistry. 81:110-117.
Rensch, C.; et al. (2013). Microfluidics: A groundbreaking technology for PET tracer production? Molecules, 18:7930-7956.
International Search Report and Written Opinion issued in PCT/GB2015/053171, dated Feb. 9, 2016, 11 pages.
Carrara et al. Multiplexing pH And Temperature in a Molecular Biosensor; Conference Paper, 2010, 4 pages.
Hamacher et al. Efficient Stereospecific Synthesis of No-Carrier-Added 2-[18F]-Fluoro-2Deoxy-D-Glucose Using Aminopolyether Supported Nucleophilic Substitution; J—Nuclear Medicine and Biology vol. 27, 1986, pp. 235-238.
Kugler et al. Optimizing the Transfer of[18F]Fluoride From Aqueous To Organic Solvents By Electrodeposition Using Carbon Electrodes Applied Radiation and Isotopes vol. 91, 2014, pp. 1-7.
Pascal et al. Dose-On-Demand of Diverse [18F] Fluorocholine Derivatives Through a Two-Step Microfluidic Approach; Nuclear Medicine and Biology vol. 38, 2011, pp. 637-644.
"Achieve Faster LC with Onyx Monolithic Silica HPLC Columns," Phenomenex, 2013, retrieved from https://phenomenex.blob.core.windows.net/documents/2791ff52-0585-4146-9c00-fbb700e390f0.pdf, 6 pages.
He et al., "Monolith-based 68Ga processing: A new strategy for purification to facilitate direct radiolabelling methods," Reaction Chemistry and Engineering, vol. 1, 2016, pp. 361-365.
Nakao et al., "Improved radiometabolite analysis procedure for positron emission tomography (PET) radioligands using a monolithic column coupled with direct injection micellar/high submicellar liquid chromatography," Talanta, vol. 113, Sep. 2013, pp. 130-134.
Tarn et al., "Positron detection in silica monoliths for miniaturised quality control of PET radiotracers," Chemical Communications, vol. 52, 2016, pp. 7221-7224.
Tarn et al., "Purification of 2-[18F]fiuoro-2-deoxy-d-glucose by on-chip solid-phase extraction," Journal of Chromatography A, vol. 1280, Mar. 2013, pp. 117-121.
Official Action for U.S. Appl. No. 15/521,204, dated Mar. 28, 2019, 11 pages. Restriction Requirement.
Official Action for U.S. Appl. No. 15/521,204, dated Jul. 29, 2019, 11 pages.
Official Action for U.S. Appl. No. 15/521,204, dated Mar. 27, 2020, 12 pages.
Official Action for U.S. Appl. No. 15/521,207, dated Oct. 11, 2018, 10 pages. Restriction Requirement.
Official Action for U.S. Appl. No. 15/521,207, dated Feb. 6, 2019, 9 pages.
Official Action for U.S. Appl. No. 15/521,207, dated Jun. 20, 2019, 10 pages.
Official Action for U.S. Appl. No. 15/521,207, dated Oct. 10, 2019, 9 pages.
Official Action for U.S. Appl. No. 15/521,207, dated Mar. 18, 2020, 8 pages.
Official Action for U.S. Appl. No. 15/521,205, dated Jul. 31, 2018, 28 pages.
Official Action for U.S. Appl. No. 15/521,205, dated Aug. 22, 2019, 36 pages.
Official Action for U.S. Appl. No. 15/521,205, dated Feb. 28, 2020, 32 pages.
Unger et al., "Chapter 3: Column Technology in Liquid Chromatography," in "Liquid Chromatography: Fundamentals And Instrumentation," (ed. Fanali et al.), Elsevier, Waltham, MA, 2013, 48 pages.

(56) References Cited

OTHER PUBLICATIONS

Official Action for U.S. Appl. No. 15/521,204, dated Oct. 5, 2020, 9 pages.
Official Action for U.S. Appl. No. 15/521,207, dated Sep. 11, 2020, 9 pages.
Official Action for U.S. Appl. No. 15/521,205, dated Nov. 20, 2020, 36 pages.
Chiu et al. "Small but Perfectly Formed? Successes, Challenges, and Opportunities for Microfluidics in the Chemical and Biological Sciences," Chem, Feb. 2017, vol. 2, pp. 201-223.
Pereiro et al. "Nip the bubble in the bud: a guide to avoid gas nucleation in microfludics," Lab Chip, 2019, vol. 19, pp. 2296-2314.
Stone et al. "Engineering Flows in Small Devices," Annual Review of Fluid Mechanics, 2004, vol. 36, pp. 381-411.
Whitesides "The origins and the future of microfluidics," Nature, Jul. 2006, vol. 442, pp. 368-373.
Official Action with English Translation for Japan Patent Application No. 2017-541173, dated Jun. 14, 2021, 9 pages.
Official Action for U.S. Appl. No. 15/521,204, dated Jun. 2, 2021 9 pages.
Kutter, "Liquid phase chromatography on microchips," Journai of Chromatography A., vol. 1221, Oct. 21, 2011, pp. 72-82.
Official Action for U.S. Appl. No. 15/521,207, dated Apr. 5, 2021, 10 pages.
Notice of Allowance for U.S. Appl. No. 15/521,205, dated Mar. 15, 2021, 6 pages.
Sadeghi et al. "Reusable electrochemical cell for rapid separation of [18F]fluoride from [18O]water for flow-through synthesis of 18F-labeled tracers," Applied Radiation and Isotopes, 2013, vol. 75, pp. 85-94.
Wong et al. "Reactivity of electrochemically concentrated anhydrous [18F]fluoride for microfluidic radiosynthesis of 18F-labeled compounds," Applied Radiation and Isotopes, 2012, vol. 70, pp. 193-199.
Notice of Allowance for U.S. Appl. No. 15/521,204, dated Mar. 15, 2022 9 pages.
Official Action for U.S. Appl. No. 15/521,207, dated Feb. 3, 2022 11 pages.
Official Action for U.S. Appl. No. 15/521,207, dated Jun. 2, 2022 11 pages.

\* cited by examiner

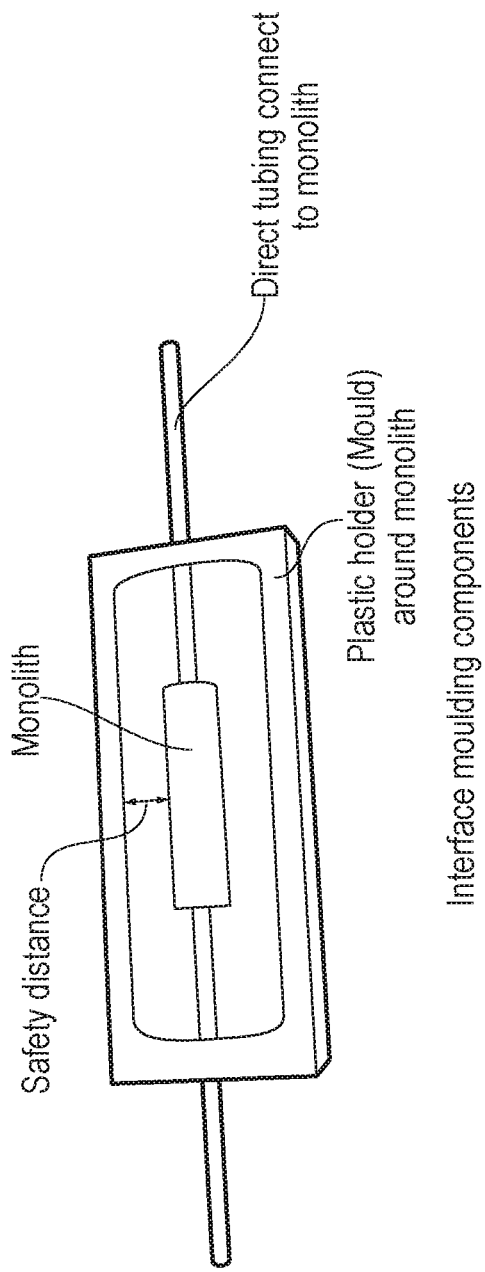
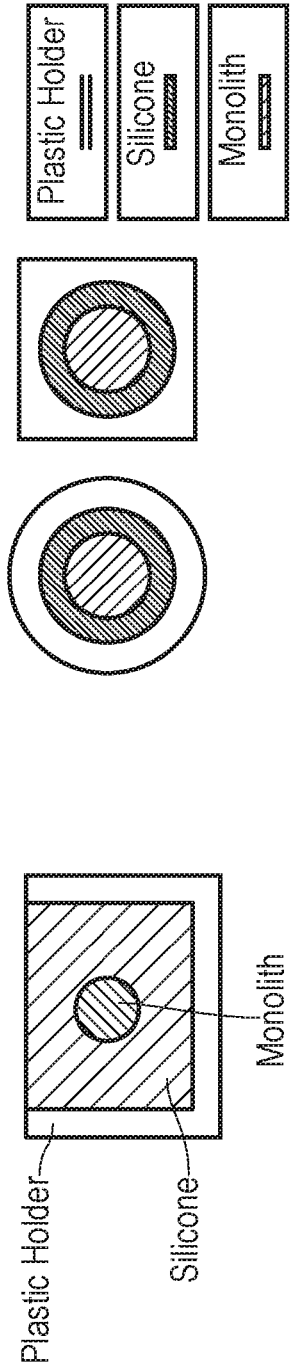
FIG. 8A
FIG. 8B
FIG. 8C

METHOD FOR SEPARATION OF RADIOACTIVE SAMPLE USING MONOLITHIC BODY ON MICROFLUIDIC CHIP

CROSS REFERENCE TO RELATED APPLICATIONS

This application is a national stage application under 35 U.S.C. 371 and claims the benefit of PCT Application No. PCT/GB2015/053171 having an international filing date of 22 Oct. 2015, which designated the United States, and which PCT application claimed the benefit of Great Britain Patent Application No. GB1418893.2 filed 23 Oct. 2014, the contents of each of which are incorporated herein by reference in their entireties.

FIELD OF THE INVENTION

The present invention relates to monolithic bodies, uses thereof and processes for the preparation thereof. Certain embodiments of the present invention relate to the use of a monolithic body in the preparation of a radioactive substance, for example a radiopharmaceutical, as part of a microfluidic flow system and a process for the preparation of such a monolithic body.

BACKGROUND TO THE INVENTION

Positron emission tomography (PET) is a powerful molecular imaging technique for the study and visualisation of the molecular and cellular processes of human physiology which can provide important information about metabolism and diseases such as cancer (Phelps, 2000; PNAS, 1; 97(16): 9226-33; Wood et al., 2007, Science, 318, 1108-1113). In addition to diagnostic applications, the use of molecular imaging techniques in drug discovery allows rapid evaluation of tissue targeting capability, bio-distribution and pharmacokinetics of both small molecules and proteins. The most common positron-emitting radioisotopes suitable for incorporation into organic structures are fluorine-18 ($^{18}F$), carbon-11 ($^{11}C$), nitrogen-13 ($^{13}N$) and oxygen-15 ($^{15}O$) (P. W. Miller, J. Chem. Technol. Biotechnol., 2009, 84, 309-315). Other halide isotopes such as $^{75}Br$, $^{76}Br$ and $^{124}I$ can be incorporated using related methodology. There have also been advances in the use of metal ions such as the generator produced $^{68}Ga$ and the longer lived $^{64}Cu$ ($t_{1/2}$=12.7 h) which require appropriate chelators for in vivo stability (Mewis and Archibald, 2010; Coord. Chem. Rev., 254, 1686-1712; Silversides et al., 2011, Dalton Trans., 40, 6289-6297).

Because of its appropriate half-life (109.8 min) allowing sufficient time for multistep synthetic labelling reactions and transportation of doses to sites several hours away, and a low positron energy giving high resolution images, $^{18}F$ has become the most widely used and commonly available radioisotope for PET imaging. Currently, 2-[$^{18}F$]fluoro-2-deoxy-D-glucose ([$^{18}F$]FDG) is the most frequently used radiopharmaceutical for PET investigations. $^{68}Ga$ is another commonly used PET radioisotope which is produced in a $^{68}Ge/^{68}Ga$ generator or a cyclotron. As an iron mimic in vivo, gallium localizes to and interacts with many processes in the body in which iron(III) is manipulated. Gallium based radiopharmaceuticals are generally administered as $^{68}Ga$ labelled peptides, produced by binding the $Ga^{3+}$ ion to bifunctional chelators. Reactions are normally rapid under mild aqueous conditions and form a complex with sufficient kinetic stability in vivo to allow imaging over several hours. Fast target localization and blood clearance make $^{68}Ga$ the radiotracer of choice in many scanning scenarios.

Historically, PET tracers were produced in large batches at centralised cyclotron or decay generator facilities and then transported as multiple doses to the imaging sites, usually a hospital, to be administered to multiple patients during pre-arranged PET clinics. However, recent technological advances mean that individual imaging sites are able to have mini-PET cyclotrons on site thus allowing small volumes of radioisotopes, such as $^{18}F$, to be produced for the on-demand synthesis of a single dose of radiotracer i.e. "dose-on-demand". Currently, the BG-75 Biomarker Generator mini-cyclotron is available from Advanced Biomarker Technologies (ABT). In an alternative scenario, the radioisotope is prepared at a centralised facility but transported to the imaging site for radiotracer production and analysis.

The use of radioactive substances as radiopharmaceuticals involves the administration of a radiopharmaceutical composition to a patient. This necessitates that the administered dose be free from potentially harmful starting materials or by-products that may be present as a result of the manufacturing process. Often the radiopharmaceutical is administered by injection, and this further necessitates that the dose be sterile, at physiological pH and free from particulate matter. With this in mind, the pharmaceutical composition must be analysed by performing stringent quality control (QC) tests on at least a sample thereof. The tests required for a specific radiopharmaceutical are listed in various pharmacopeia monographs, which detail the techniques/instrumentation to be used and the limits allowed for the different molecules present in a dose. Different pharmacopeias' are available for different geographical regions and these include the European Pharmacopeia (EP) ($8^{th}$ Edition, EDQM Council of Europe, Strasbourg, 2013), the British Pharmacopeia (BP) (2012, TSO, Norwich, 2012), the International Pharmacopeia (Ph. Int.) published by the World Health Organization (WHO) ($4^{th}$ Edition, Pharmacopoeia Internationalis Edito Quarta—third supplement, Geneva, 2013), the United States Pharmacopeia (USP) ($37^{th}$ Edition) and National Formulary ($32^{nd}$ Edition) (USP-NF), and the Chemistry, Manufacturing and Controls (CMC) Guidance published the US Food and Drug Administration (FDA) (Silver Spring 2011).

In all of these scenarios, manipulation of very small quantities for radiopharmaceutical production and analysis is necessary, for example in the nanolitre to microliter scale. This nanolitre to microlitre scale is often the best approach to give both efficient transfer and synthetic procedures. With regard to radiopharmaceutical preparation, the extremely high surface-to-volume ratio and small size of microreactors combined with flow chemistry have significant potential to facilitate such chemistry in terms of higher yields, shorter reaction times, reduced consumption and lower environmental impact. The validity of the miniaturized approach to perform fast and high yield radiolabelling reactions has been demonstrated in several pioneering works. However, such work is challenging because it is carried out at extremely low concentrations, often with levels of contaminants and/or impurities comparable to that of the reagents (Li and Conti, 2010, Adv. Drug. Deliv. Rev; August 30; 62(11):1031-51). Separation of radioactive material from a sample, whether it be separation for concentration, separation for purification, separation for a synthetic purpose or separation for analysis, is thus a critical process step whereby any marginal gain or loss will have a dramatic effect upon the overall process yield and efficiency.

There is an ongoing need for improved preparative methods with regard to synthetic and/or analytical methods in this field.

The use of monolithic columns in preparative and analytical liquid chromatography is known (see for example US patent application number US 2008/0093300). Monolithic columns, in contrast to traditional high performance liquid chromatography (HPLC) columns that comprise packed particles, often contain a single solid structure comprising open pores that together form a network of channels as the stationary phase. Monolithic columns have been used in HPLC, and have also been used in flow-through microfluidic devices for the concentration, solvent exchange and activation of [$^{18}$F]fluoride.

WO 2013/188446A1 discloses methods to exchange and activate [$^{18}$F]fluoride on a flow through microfluidic chip using a polymer based monolith, specifically a poly(vinylbenzyl chloride-co-divinylbenzene) monolith structure. A similar disclosure is also made in Ismail et al. (RSC Adv., 2014, 4, 25348-25356) which discloses a polymer based monolith [polystrene-imidazolium (PS-Im+Cl-) monolith] within a flow-through microfluidic chip for the concentration, solvent exchange and activation of [$^{18}$F]fluoride.

It would be advantageous if microfluidic manipulation of radioactive substances could be carried out using inorganic monoliths rather than polymer monoliths. Inorganic monoliths such as silica monoliths have good solvent resistance and high mechanical stability. It is also believed that the use of inorganic monoliths is less likely to result in contamination of the radioactive substance with fabrication materials compared to polymer monoliths and particulate chromatographic systems. Particular chromatographic systems often suffer from leaking or blockage problems due to a build-up of pressure (back pressure) and it is believed that these problems may be partially or wholly mitigated by the use of inorganic monoliths.

The inventors have also been successful in overcoming a number of technical challenges that were faced during the fabrication of microfluidic systems which make use of inorganic monoliths. For example it is very difficult to prepare silica-based monoliths within microfluidic channels using a sol-gel process as shrinkage and heat-bonding can cause damage such as cracking to the monolith. Silica monoliths for use in flow systems where no leakage is essential have previously been prepared and set in a removable mould, once set, the monolith has been removed from the mould and then clad in heat shrinkable Teflon tube (Fletcher et al., J Porous Mater., 2011, 18, 501-508).

Unexpectedly and surprisingly, it has been found that the use of a chromatographic inorganic monolithic body in the preparation of a radioactive substance, for example a radiopharmaceutical, as part of a microfluidic device results in a higher yielding and/or more efficient manufacturing process.

The inventors have also been successful in incorporating an inorganic chromatographic monolithic body into a microfluidic flow system. Due to the miniaturized scale of microfluidic devices, the inclusion and use of a monolithic body in a microfluidic flow system presented many technical challenges that have been overcome by the inventors. In particular, the inventors have developed a novel process for the manufacture of a monolithic body in the form of a monolithic module for incorporation into a microfluidic flow system.

Certain embodiments of the present invention aim to at least partially mitigate the problems associated with the prior art.

Summary of Certain Embodiments of the Invention

It is an aim of certain embodiments of the present invention to provide, and there is provided herein, the use of a chromatographic monolithic body to separate an analyte from a sample wherein the sample contains a radioactive substance and wherein the monolithic body is an inorganic monolithic body and is part of a microfluidic flow system. For example, the monolithic body may be part of a monolithic module.

It is believed this aspect of the invention may be advantageous because there is less potential for contamination of the monolithic body and thus less potential for contamination transfer from the monolithic body, and/or because there is less potential for failure of the monolithic body, for example failure as a result of leakage from or blockage in the monolithic body or microfluidic flow system, and/or because more efficient separation may be achieved. Other advantages may also be envisaged.

It is an aim of certain embodiments of the present invention to provide, and there is provided herein, a process for separating an analyte from a radioactive sample, which process comprises the step of:
  a) eluting the sample through a chromatographic monolithic body;
wherein the monolithic body is an inorganic monolithic body and is part of a microfluidic flow system. For example, the monolithic body may be part of a monolithic module.

It is believed that this aspect of the invention is advantageous because there is less potential for contamination of the monolithic body and thus less potential for contamination transfer from the monolithic body, and/or because there is less potential for failure of the monolithic body, for example failure as a result of leakage from or blockage in the monolithic body or microfluidic flow system, and/or because more efficient separation may be achieved. Other advantages may also be envisaged.

It is an aim of certain embodiments of the present invention to provide, and there is provided herein, a process for preparing a radiopharmaceutical comprising the steps of:
  i) concentrating a radioisotope;
  ii) optionally, where necessary, activating the radioisotope, for example by solvent exchange;
  iii) synthesizing the radiopharmaceutical, for example by labelling a non-radioactive analogue of the radiopharmaceutical with the radioisotope;
  iv) purifying the radiopharmaceutical; and
  v) analysing the radiopharmaceutical;
wherein at least one of steps i), ii) iii), iv) and v) comprises a process for separating an analyte from a radioactive sample. The process for separating an analyte from a radioactive sample comprises the step of:
  a) eluting the sample through a chromatographic monolithic body;
wherein the monolithic body is an inorganic monolithic body and is part of a microfluidic flow system. For example, the monolithic body may be part of a monolithic module.

It is an aim of certain embodiments of the present invention to provide, and there is provided herein, a process for the manufacture of a monolithic module comprising the steps of:
  i) supplying a mould for injection moulding containing an inorganic monolithic body;
  ii) injecting liquid polymer into the mould wherein the liquid polymer flows between a surface of the mould and a surface of the monolithic body and surrounds the monolithic body; and iii) setting the polymer to form the monolithic module.

The process for the manufacture of a monolithic module may further comprise, where necessary, the step of annealing the monolithic mould. It is believed that annealing the monolithic module may release any residual stress induced during the moulding process.

It will be appreciated that many of the terms and phases used within this specification will be known to the person skilled in the art. Definitions provided herein are intended as embodiments of the invention separately and in any combination with any other embodiments and/or definitions herein.

As used herein, an "analyte" is one or more substance(s) to be selected out of or separated from a sample. When an analyte is separated from a sample by a chromatographic body, it may be retained on the body or it may elute more slowly through the body than other substance(s) in the sample. An analyte may be a substance of interest, for example a compound or isotope of interest, or it may be an impurity to be removed from a composition of substances. In some embodiments, an analyte may be a reactant.

As used herein, the "sample" is the material to be investigated or analysed by a chromatographic method. The sample may comprise a single component of a mixture of components. The sample comprises the analyte and optionally other substances from which the analyte is to be separated. In some embodiments, a sample may comprise a reactant and may be eluted through a chromatographic monolithic body to effect a chemical reaction, for example a solid phase chemical reaction on the surface of the monolithic body.

As used herein, the "eluent" is the solvent that carries the analyte and any substances that the analyte is to be separated from. The eluent carries the sample.

As used herein, the "eluate" is the mobile phase flowing out of the chromatographic body, in particular, after the analyte has been separated from the sample.

As used herein, the "mobile phase" comprises the phase that flows through the chromatographic body. The mobile phase comprises the sample dissolved in the eluent and flows into the chromatographic body.

A fluid flow can be described as "microfluidic" (i.e. "microfluidic fluid flow") if a fluid passes through a channel having at least one dimension of less than 1 mm, in particular a channel having a dimension of less than 1 mm, e.g. less than 500 µm, e.g. less than 250 µm, e.g. less than 200 µm, or e.g. less than 150 µm. This creates laminar flow characteristics (generally having a Reynolds number of less than 100) where diffusion is the dominant cross stream chemical interaction. Consequently, microfluidic fluid flow occurs during the manipulation of small volumes, for example from 1 nl to 100 µl, within microstructured devices that features dimensions of the order of 10's to 100's µm.

As used herein, a "microfluidic flow system" comprises a system having at least one channel for fluid flow, the channel having at least one dimension of less than one 1 mm, for example less than 500 µm, e.g. 300 µm or less, e.g. 200 µm or less, e.g. 150 µm or less, e.g. 100 µm or less, e.g. 50 µm or less. The microfluidic flow system comprises a microfluidic device but may also comprise other components that are in fluid communication with the microfluidic device.

In one embodiment, the system comprises one or more channels having a width of, for example, between about 100 µm to about 200 µm e.g. about 150 µm and a depth of for example between about 40 µm and about 60 µm, for example about 50 µm deep.

A "microfluidic device" can be identified by the fact that it has one or more channels with at least one dimension less than 1 mm for example less than 0.5 mm, for example with width of 0.2 mm to 0.3 mm and depth of 0.2 mm to 0.3 mm, in particular a channel having a dimension of less than 1 mm, for example width and depth 0.25 mm. The microfluidic device may be part of a microfluidic flow system.

As used herein, a "bio chip" refers to a device which can be used for synthetic or analytical purposes for samples having a volume of from about 10 nl to about 10 ml. In one embodiment, the bio chip is used to process, synthesize and/or analyze samples having a volume of between about 0.1 ml and 2 ml. In one embodiment, the bio chip is a microfluidic device.

A "microfluidic chip" can be identified by the fact that it has one or more channels with at least one dimension less than 1 mm, for example, less than 500 µm, e.g. 300 µm or less, e.g. 200 µm or less, e.g. 150 µm or less, e.g. 100 µm or less, e.g. 50 µm or less, in particular a channel having a dimension of less than 1 mm, e.g. for example, between about 100 µm to about 200 µm e.g. about 150 µm and a depth of for example between about 40 µm and 60 µm, for example about 50 µm deep. The microfluidic chip may be part of a microfluidic flow system. The one or more channels may form a fluid flow path in the chip.

As used herein, the term "microfluidic chip" refers to a device which can be used for synthetic or analytical purposes for samples having a volume of from about 10 nl to 10 ml. In one embodiment, the microfluidic chip is used to process, synthesize and/or analyze samples having a volume of between about 0.1 ml and 2 ml e.g. about 1 ml or less e.g. 0.5 ml.

In one embodiment, the microfluidic chip is a microfluidic device and/or is comprised within a microfluidic device. In certain embodiments, the microfluidic chip may comprise one or more separable modular components e.g. components comprising an electrochemical (EC) cell and the like. Aptly, the modular component may comprise a detection zone.

The Reynolds number which is used to characterise microfluidic flow (i.e. the flow of a fluid through a microfluidic channel is calculated according to equation 1:

$$Re = \frac{LV_{avg}\rho}{\mu} \qquad \text{equation 1}$$

wherein:

L is the most relevant length scale; $\rho$ is the viscosity; $\rho$ is the fluid density; and $V_{avg}$ is the average velocity of the flow.

For many microchannels:

$$L = 4A/P \qquad \text{equation 2}$$

wherein:

A is the cross sectional area of the channel; and P is the wetted perimeter of the channel.

Due to the small dimensions of the channels in a microfluidic device, $R_e$ is usually less than 100, in particular less than 1.0. Fluid flow with a Reynolds number of this magnitude is completely laminar with very little or no turbulence such that molecular transport is relatively predictable.

As used herein, a "monolithic body" or "monolith" is a single solid structure comprising open pores which pores together form an interconnected network of channels. In one embodiment, a monolithic body is single solid structure comprising a bimodal pore structure wherein the pores comprise macropores and mesopores. In one embodiment, within the single solid structure, open macropores together form an interconnected tortuous network of channels and mesopores produce a high functional surface area. The monolithic body may be shaped in the form of a column, a tube, a rod, a disc or the like. In one embodiment the monolithic body is in the shape of a cuboid. In one embodiment, the monolithic body is in the shape of a cylinder. In one embodiment, the monolithic body comprises a silica-based composition, for example silica, for example functionalised silica. In another embodiment, the monolithic body comprises a mesoporous gel which gel may be partially or completely pyrolysed to form a ceramic material, for example the monolithic body may comprise silicon diimide mesoporous gel which is optionally partially pyrolysed to form a silicon imido nitride, or completely pyrolysed to form a silicon nitride ceramic material. A monolithic body referred to herein is inorganic. Typically the monolithic body of the invention is highly porous.

Typically the monolithic body has a high surface area, for example at least 100 m$^2$/g, in particular at least 150 m$^2$/g and more particularly 100 to 300, e.g. 100 to 250 m$^2$/g, for example 150 to 200 m$^2$/g.

A monolithic body may be prepared using a sol-gel procedure. For example, a polymer such as PEO (polyethylene oxide) is added to an aqueous solution of acid, cooled and stirred. Silicon alkoxide (for example TEOS) is added with stirring to form a transparent solution. This solution is injected into a mould and heated (for example 40° C., 3 days) to form a wet semi-solid gel monolith. The gel is removed from the mould, washed with water and then added to ammonium hydroxide for further post-treatment (for example 90° C., 16 hours). The monoliths are washed and dried (for example 40° C., 1 day).

Standard monolithic HPLC columns are commercially available for example from organisations such as Phenomenex, Merck, Thermo Scientific and Agilient.

As used herein, a "monolithic module" comprises one or more monolithic body/bodies hermetically sealed in a unit comprising at least one inlet and at least one outlet. The monolithic module may be adapted for incorporation into a monolithic flow system. The monolithic module may be prepared by an injection moulding process, for example as described herein. The monolithic body is inorganic.

As used herein, a "micropore" is a pore having a pore diameter of less than 2 nm, in particular between 0.1 nm and 2 nm.

As used herein, a "mesopore" is a pore having a pore diameter of between 2 nm and 50 nm.

As used herein, a "macropore" is a pore having a pore diameter of greater than 50 nm, in particular between 50 nm and 1 μm.

As used herein, a "radiopharmaceutical" is an isotopically labelled analogue of a pharmaceutical molecule, wherein the isotope label is radioactive. A radiopharmaceutical can be used for diagnostic or therapeutic purposes.

As used herein, a "radiotracer" is a radiopharmaceutical having a largely unaltered metabolic pathway compared to the unlabelled analogue. It is therefore possible to follow and quantify processes on a particular metabolic pathway by detecting the radioactive decay of the labelling radioisotope. Radiotracers are used for diagnostic purposes.

Examples of radiotracers include, but are not limited to, $^{18}$F-FLT ([$^{18}$F]fluoro thymidine), $^{18}$F-FDDNP (2-(1-{6-[(2-[$^{13}$F]fluoroethyl)(methyl)amino]2-naphthyl}ethylidene)malonitrile), $^{18}$F-FHBG (9-[4-[$^{18}$F]fluoro-3-(hydroxymethyl) butyl]guanine or [$^{18}$F]-penciclovir), $^{18}$F-FESP ([$^{13}$F]-fluoroethylspiperone), $^{18}$F-p-MPPF (4-(2-methoxyphenyl)-I-[2-(N-2-pyridinyl)-p-[$^{18}$F]fluorobenzamido] ethylpiperazine), $^{18}$F-FDG (2-[$^{18}$F]fluoro-2-deoxy-D-glucose), $^{18}$F-FMISO ([$^{18}$F]fluoromisonidazole) and $^{18}$F-sodium fluoride.

$^{18}$F-FDG or [$^{18}$F]FDG is a radiolabelled sugar molecule. When used with PET imaging, images are produced that show the metabolic activity of tissues. In FDG-PET scanning, the high consumption of the sugar by tumour cells, as compared to the lower consumption by normal surrounding tissues, identifies these cells as cancer cells. FDG is also used to study tumour response to treatment. As used herein, the term FDG relates to the compound 2-fluoro-2-deoxy-D-glucose and the term $^{18}$F-FDG or [$^{18}$F]FDG relates to radiolabelled (2-[$^{18}$F]fluoro-2-deoxy-D-glucose.

Sodium fluoride is an imaging agent for PET imaging of new bone formation. It can assess changes both in normal bone as well as bone tumours. As a result, it can be used to measure response to treatment.

$^{18}$F-FLT or [$^{18}$F]FLT is a radiolabeled imaging agent that is being investigated in PET imaging for its ability to detect growth in a primary tumour. Studies may also measure the ability of FLT with PET to detect tumour response to treatment.

$^{18}$F-FMISO or [$^{18}$F]FMISO is an imaging agent used with PET imaging that can identify hypoxia (low oxygen) in tissues. Tumours with low oxygen have been shown to be resistant to radiation and chemotherapy.

Alternatively, the radiotracer is a radiopharmaceutical which incorporates a radioisotope selected from the group consisting of $^{11}$C, $^{68}$Ga and $^{64}$Cu.

Further examples of radiotracers include any which use bifunctional chelators to form conjugates of $^{68}$Ga-DOTA, $^{68}$Ga-NOTA and $^{68}$Ga-DTPA with peptides, antibodies and other targeting vectors. Examples of $^{68}$Ga based radiotracers include $^{68}$Ga-DOTA-TATE and $^{68}$Ga-DOTA-TOC which can be used to image neuroendocrine tumours through recognition of somatostatin receptors.

$^{68}$Ga-NOTA-bis (phosphonate) is PET radiotracer for bone imaging, $^{68}$Ga-DOTATOC is a PET radiotracer for imaging in patients with meningioma.

$^{68}$Ga-DOTATATE is a PET radiotracer for imaging in patients with malignant phaeochromocytomas.

K222 is Kryptofix 2.2.2, referred to as "aminopolyether" in the BP. It is usually the phase transfer catalyst of choice in the synthesis of [$^{18}$F]FDG by nucleophilic substitution. However, other catalysts such as tetrabutylammonium and 4-(4-methylpiperidin-1-yl)pyridine could be employed and are included in the BP.

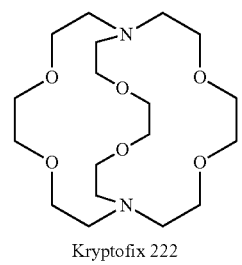 [SMILES: C1COCCN2CCOCCOCCN(CCO1)CCOCCOCC2]

Kryptofix 222

DOTA is 1,4,7,10-tetraazacyclododecane-1,4,7,10-tetraacetic acid.
DTPA is diethylene triamine pentaacetic acid.
NOTA is 1,4,7-triazacyclononane-1,4,7-triacetic acid.

CIDG is 2-chloro-2-deoxy-D-glucose. CIDG is an impurity that can be present particularly when using acid hydrolysis in which a chloride atom takes the place of the [$^{18}$F]fluoride label. A further source of chloride may be an anion exchange cartridge used to pre-concentrate the [$^{18}$F] fluoride label in many systems, depending on the counter ion present on the cartridge resin.

ACY-[$^{18}$F]FDG refers to the acetylated/unhydrolysed form of [$^{18}$F]FDG, which is 2-[$^{18}$F]fluoro-1,3,4,6-tetra-O-acetyl-D-glucose (also referred to as [$^{18}$F]TAG), while partially hydrolysed ACY-[$^{18}$F]FDG can also be present.

[$^{18}$F]FDM is 2-[$^{18}$F]fluoro-2-deoxy-D-mannose, a byproduct that can be produced during the [$^{18}$F]FDG synthesis process, and which can also be present in fully or partially hydrolysed form (ACY-[$^{18}$F]FDM).

As used herein, a "radiopharmaceutical composition" comprises a radiopharmaceutical, or a pharmaceutically acceptable salt thereof, in association with a pharmaceutically acceptable adjuvant, diluent or carrier. In one embodiment, a radiopharmaceutical composition may comprise the radiopharmaceutical and an isotonic saline solution.

The preparation of a radiopharmaceutical, for example a radiotracer, may comprise the following steps:

i) separation of a radioisotope from a sample;

ii) where necessary, activation of the radioisotope, for example by solvent exchange;

iii) synthesis of the radiopharmaceutical, for example a radiotracer;

iv) separation of the radiopharmaceutical, for example a radiotracer, from a reaction mixture;

v) formulation of radiopharmaceutical into a radiopharmaceutical composition, for example a radiotracer formulated with an isotonic saline solution;

vi) analysis of the radiopharmaceutical composition (quality control).

In step i) separation is carried out to concentrate the radiotracer from the sample. In step ii) activation of the radioisotope can be achieved by separating the radioisotope from a solvent and replacing said solvent with another solvent. In step iii), one reactant may be separated and retained on the monolithic body for further reaction with additional reagents. In step iv), separation is carried out to purify the radiopharmaceutical from the reaction mixture. Analysis of the radiopharmaceutical composition, for example as in step vi) above may also be referred to as a "quality control" step. Aptly, the monolithic body may be utilised in one or more of steps (i) to (vi).

For example, the synthesis of [$^{18}$F]FDG is shown schematically below:

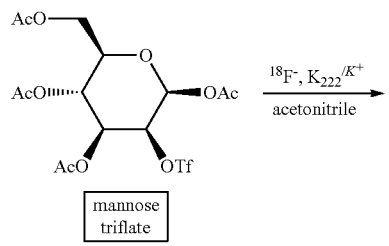

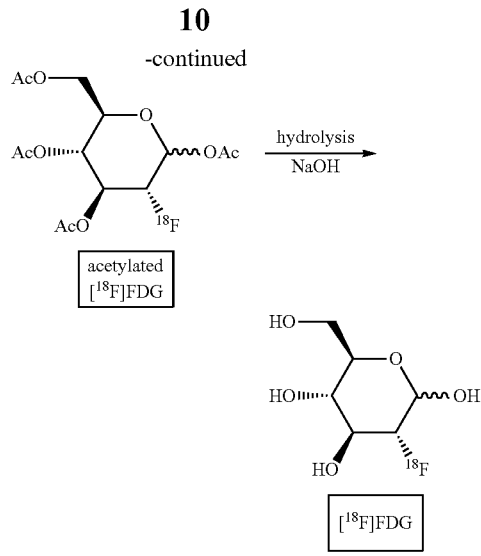

While [$^{18}$F]FDG was originally synthesised by electrophilic substitution, nowadays it may be produced by the nucleophilic substitution of Hamacher et al (K. Hamacher, H. Coenen, G. Stöcklin, *J. Nucl. Med.*, 1986, 27, 235-238). Aptly, the procedure follows the steps of:

1. [$^{18}$F]fluoride generation by proton bombardment of $^{18}$O-enriched cyclotron via a cyclotron;
2. Pre-concentration of aqueous [$^{18}$F]fluoride, for example using an ion exchange column, using a monolithic body or by electrochemical trapping.
3. Release of [$^{18}$F]fluoride in acetonitrile containing addition of phase transfer catalyst (typically Kryptofix 2.2.2) and potassium carbonate.
4. Radiolabelling reaction of mannose triflate with [$^{18}$F] fluoride via $S_N2$ nucleophilic substitution, producing the acetylated form of [$^{18}$F]FDG (i.e. unhydrolysed [$^{18}$F]FDG).
5. Solvent exchange from acetonitrile to water.
6. Hydrolysis of acetylated-[$^{18}$F]FDG to [$^{18}$F]FDG, either by acid hydrolysis (HCl) or base hydrolysis (NaOH).
7. Purification of the crude [$^{18}$F]FDG mixture, e.g. via solid-phase extraction (SPE), for example using a monolithic body.
8. Formulation of the [$^{18}$F]FDG dose as an isotonic saline (sodium chloride) solution.

For the avoidance of doubt "separate" as used herein means the separation or removal of an analyte from a sample, for example, for the purposes of concentration, purification, synthesis and/or analysis.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Further details of certain embodiments are provided below.

In one embodiment, the monolithic body is inorganic and is comprised as part of a monolithic module as defined herein. A monolithic module comprises an inorganic monolithic body within an injection moulded polymer. The monolithic module comprises an inlet and an outlet.

In one embodiment, the monolithic body comprises a composition selected from a silicon based composition, an aluminium based composition and a titanium based composition, wherein each composition is optionally chemically functionalised. In particular, the composition is selected from a silica based composition, an alumina based composition and a titania based composition, wherein each composition is optionally chemically functionalised. In another embodiment, the monolithic body comprises a silicon based composition selected from silica, silicon imido nitride, silicon imide and silicon nitride, wherein each composition is optionally chemically functionalised. In particular, the monolithic body comprises silica or chemically functionalised silica. Processes for the chemical functionalization of silicon (for example silica), aluminium (for example alumina) and titanium (for example titania) based monolithic bodies are known to the person skilled in the art. Chemically functionalized silicon is also commercially available, for example commercially available from Water Corporation, Sigma-Aldrich, SiliCycle Inc. etc.

In one embodiment, the monolithic body is a cation exchange monolithic body, for example the monolithic body comprises silica modified with propyl sulfonic acid groups. In another embodiment, the monolithic body is an anion exchange monolithic body, for example the monolithic body comprises silica modified with quaternary ammonium. In another embodiment, the monolithic body is a reverse phase monolithic body, for example the monolithic body comprises silica modified with octadecyl carbon groups (C18 or C18 monolithic body).

In one embodiment, the monolithic body is between 10 mm to 80 mm in length, for example 10 mm to 40 mm, for example 36 mm in length. In one embodiment, the monolithic body has a width of 2 mm to 6 mm, for example 3 mm to 5 mm in diameter, for example 4 mm in diameter.

In one embodiment, the analyte is a radioisotope or cation or anion thereof. A radioisotope may have been produced in a cyclotron or a decay generator. The monolithic body is used to isolate the radioisotope or anion or cation thereof from the radioactive solution produced by the cyclotron or decay generator. The sample may be the radioactive solution produced by a cyclotron or decay generator. The analyte may be radioactive isotope [$^{18}$F]fluoride, (for example $^{18}$F$^{-}$) or the analyte may be radioactive isotope $^{68}$Ga or cation thereof (for example $^{68}$Ga$^{3+}$). In this embodiment, separation is carried out to concentrate the radiotracer from the sample (step i).

Where the analyte is a radioisotope for example $^{68}$Ga, an aqueous radioactive substance, for example $^{68}$Ga solution, is passed through a cation-exchange monolithic body and $^{68}$Ga is trapped in the monolithic body. The monolithic body is then washed with an organic based solution followed by elution with a small volume of organic based solution to release the $^{68}$Ga. Labelling/or synthesis of a gallium based radiotracer is performed by addition of the reagent to the obtained solution and the reaction mixture is passed through a reverse phase monolithic body (for example C18 monolithic body) for purification.

Synthesis of the radiopharmaceutical (step iii) comprises reaction of the radioisotope with a non-radioactive analogue of the radiopharmaceutical or a precursor or a protected form thereof. The reaction may be effected on the monolithic body and so, in one embodiment, the synthesis step may comprise a process for separating an analyte from a radioactive sample comprising the step of eluting the sample through a chromatographic monolithic body, wherein the monolithic body is an inorganic body and is part of a microfluidic flow system. The sample comprises the radioisotope. Elution of the non-radioactive analogue of the radiopharmaceutical or a precursor or protected form thereof, may precede or follow elution of the sample comprising the radioisotope. This reaction may yield the radiopharmaceutical or a protected form thereof.

Where necessary, synthesis of the radiopharmaceutical may require a deprotection step, for example to deprotect the protected form of the radiopharmaceutical. For example, the protected form may be an acetylated form and deprotection may be effected by hydrolysis.

In one embodiment, deprotection (for example hydrolysis) may be effected by eluting a sample through a monolithic body wherein the monolithic body is an inorganic monolithic body and is part of a microfluidic flow system.

In one embodiment, the analyte is activated radioisotope, for example [$^{18}$F]fluoride activated with K222 in acetonitrile. Radiolabelling of mannose triflate with [$^{18}$F]fluoride in the presence of K222 and acetonitrile occurs in a two step process (as shown schematically herein). In the first step, reaction of mannose triflate with [$^{18}$F]fluoride in the presence of K222 and acetonitrile yields acetylated-[$^{18}$F]FDG. This step may be performed using a monolithic body by eluting a sample comprising [$^{18}$F]fluoride through a monolithic body wherein [$^{18}$F]fluoride is the analyte, and then eluting the reagents to react with [$^{18}$F]fluoride. Alternatively, a solution comprising mannose triflate as the analyte may be eluted through the monolithic body followed by the reagents to react with mannose triflate.

In one embodiment, the analyte is a radiopharmaceutical precursor or protected form thereof (for example acetylated [$^{18}$F]FDG) and the sample is a reaction mixture. For example the sample may comprise one or more or all of the components selected from acetylated [$^{18}$F]FDG, mannose triflate, radioisotope [$^{18}$F]fluoride, K222, potassium or cation thereof and acetronitrile. The product obtained in the first step is acetylated [$^{18}$F]FDG which may then be deprotected, for example by hydrolysis, to yield [$^{18}$F]FDG. Deprotection may be achieved by eluting the monolithic body, comprising the analyte acetylated [$^{18}$F]FDG, with sodium hydroxide.

In one embodiment, the analyte is a radiopharmaceutical, for example a radiotracer selected from $^{18}$F-FLT ([$^{18}$F]fluoro thymidine), $^{18}$F-FDDNP (2-(I-{6-[(2-[$^{13}$F]fluoroethyl) (methyl)amino]2-naphthyl}ethylidene)malonitrile), $^{13}$F-

FHBG (9-[4-[$^{18}$F]fluoro-3-(hydroxymethyl)butyl]guanine or [$^{18}$F]-penciclovir), $^{18}$F-FESP ([$^{18}$F]fluoroethylspiperone), $^{18}$F-p-MPPF (4-(2-methoxyphenyl)-I-[2-(N-2-pyridinyl)-p-[$^{18}$F]fluorobenzamido]ethylpiperazine), $^{18}$F-FDG (2-[$^{18}$F]fluoro-2-deoxy-D-glucose), $^{18}$F-FMISO ([$^{18}$F]fluoromisonidazole) and $^{18}$F-sodium fluoride. Separation is carried out to purify the radiotracer (step iv).

In one embodiment, the analyte is an impurity and the sample is a solution of radiotracer. Separation is carried out to purify the radiotracer (step iv).

Details of the monolithic body which may be used to remove certain impurities from a radiotracer solution are provided in the following table:

| Type of resin | Removal of: |
| --- | --- |
| Cation (+ve ion) exchange | Cationic impurities<br>Kryptofix 2.2.2<br>Metal radionuclides<br>NaOH (neutralisation) |
| Anion (−ve ion) exchange | Anionic impurities<br>Complexed metal radionuclides<br>HCl (neutralisation) |
| Normal phase (alumina) | Polar impurities<br>[$^{18}$F]fluoride<br>Bacterial endotoxins |
| Reversed phase | Non-polar impurities<br>Acetylated-[$^{18}$F]FDG<br>Acetylated-[$^{18}$F]FDM<br>Acetylated-CIDG<br>Kryptofix 2.2.2 |

For example, the analyte is an impurity selected from [$^{18}$F]fluoride and endotoxin. The monolithic body used herein is, for example, a normal phase monolithic body (for example comprising alumina or silica). For example, the analyte is an impurity selected from acetylated [$^{18}$F]FDG, acetylated [$^{18}$F]FDM, acetylated-CIDG, mannose triflate and K222. The monolithic body used herein may be a reverse phase monolithic body (for example comprising silica modified with octadecyl carbon). For example, the analyte is an impurity selected from K222 and sodium hydroxide. The monolithic body used herein may be a cation exchange monolithic body (for example silica modified with propyl sulfonic acid groups). For example, the analyte is an impurity selected from hydrochloric acid. The monolithic body as used herein may be an anion exchange monolithic body (for example silica modified with quaternary ammonium).

In one embodiment, the analyte is selected from [$^{18}$F]fluoride, [$^{18}$F]acetylated-FDG and [$^{18}$F]FDG. The monolithic body used herein may be a normal phase monolithic body (for example comprising alumina or silica) For example, the analyte may comprise analyte components [$^{18}$F]fluoride, [$^{18}$F]acetylated-FDG and [$^{18}$F]FDG and the analyte components are separated from each other by the monolithic body. The mobile phase may comprise acetonitrile and water, for example in a ratio of acetonitrile:water between for example 90:10 to 95:5, for example 90:10 or 95:5.

In one embodiment, the analyte is selected from [$^{18}$F]fluoride, [$^{18}$F]acetylated-FDG and [$^{18}$F]FDG. The monolithic body used herein may be a reverse phase monolithic body. For example the monolithic body may comprise silica modified with octadecyl carbon groups (C18 or C18 monolithic body). For example, the analyte may comprise analyte components [$^{18}$F]fluoride, [$^{18}$F]acetylated-FDG and [$^{18}$F]FDG and the analyte components are separated from each other by the monolithic body. The mobile phase may comprise acetonitrile and water, for example in a ratio of acetonitrile:water between for example 40:60 to 60:40 for example about 50:50.

In one embodiment, the analyte is selected from D-mannose, D-glucose, [$^{18}$F]FDG, [$^{18}$F]FDM and CIDG. The monolithic body used herein may be a strong anion exchange (SAX) monolithic body. For example, the analyte comprises analyte components [$^{18}$F]FDG, [$^{18}$F]FDM and [$^{18}$F]FDG and the analyte components are separated from each other by the monolithic body. The sample may comprise one or more component selected from [$^{18}$F]FDG, [$^{18}$F]FDM, [$^{18}$F]FDG, acetonitrile and water. The mobile phase may comprise sodium hydroxide, for example, 10 to 200 mM, for example 20 to 100 mM, for example 50 mM.

In one embodiment there is provided a process for the manufacture of a monolithic module comprising the steps of:
i) supplying a mould for injection moulding containing an inorganic monolithic body;
ii) injecting liquid polymer into the mould wherein the liquid polymer flows between a surface of the mould and a surface of the monolithic body and surrounds the monolithic body; and
iii) setting the polymer to form the monolithic module.

The process for the manufacture of a monolithic module may further comprise, where necessary, the step of annealing the monolithic module. It is believed that annealing the monolithic module may release any residual stress induced during the moulding process. Annealing may involve heating the monolithic module, for example in a furnace. The temperature required for annealing will depend on the polymer used and as such will be known to a person skilled in the art.

The process for the manufacture of a monolithic module may further comprise the step of providing the monolithic module with an inlet and outlet. The inlet and outlet extend between the surface of the monolithic body and the outer surface of the monolithic module. The inlet and/or outlet may be provided by machining the monolithic module, for example by drilling or milling. The monolithic module may be machined after setting the polymer and, if present, before or after the annealing step. In one embodiment, the inlet and/or outlet may be provided during the injection step by using a mould adapted to provide an inlet and/or outlet. In one embodiment, the inlet and/or outlet accommodates polyether ether ketone (PEEK) finger tight fittings slotted inside rubber syringe plunger ends.

In one embodiment, the step of i) supplying a mould for injection moulding containing an inorganic monolithic body may comprise the additional step of inserting the inorganic monolithic body into the mould for injection moulding.

In step ii) of the process for the manufacture of a monolithic module, the injected liquid polymer flows between the surface of the mould and the surface of the monolithic body and effectively surrounds the monolithic body, except for any area of contact between the mould and the monolithic body. The mould may be adapted such that the area of contact between the mould and the monolithic body defines an inlet and/or outlet. If the area of contact does not define an inlet and/or outlet, an additional step or steps may be necessary to form the monolithic module. For example, a process for the manufacture of a monolithic body may comprise the steps of:

i) supplying a mould for injection moulding containing an inorganic monolithic body;
ii) injecting liquid polymer into the mould wherein the liquid polymer flows between a surface of the mould and a surface of the monolithic body and surrounds the monolithic body, except for the area of contact between the mould and monolithic body;
iii) setting the polymer to form a partial monolithic module;
iv) inserting the partial monolithic module into a second mould for injection moulding;
v) injecting liquid polymer into the mould wherein the liquid polymer flows between a surface of the mould and an exposed surface of the monolithic body to further surround the monolithic body;
vi) setting the polymer to form the monolithic module.

This process may further comprise the steps of:
vii) optionally, where necessary annealing the monolithic unit;
viii) optionally where necessary, providing an inlet and/or outlet, for example by machining.

In certain embodiments, a second step of injecting liquid polymer into the mould may enhance adhesion between the monolithic body and the module and therefore enhance the hermetic seal.

Where a chemically functionalised monolithic body is required, a functionalised monolithic body can be used from the beginning of the process for the manufacture of a monolithic body, for example by supplying a mould for injection moulding containing a functionalised inorganic monolithic body. Alternatively, the monolithic body may be functionalised as part of the monolithic module by passing functionalization reagents through the monolithic module.

In one embodiment, the liquid polymer comprises a polymer selected from cyclic olefin copolymer (COC), cyclic olefin polymer (COP) and poly(methyl methacrylate) (PMMA). Other similar liquid polymer suitable for injection moulding may also be used. Examples of other polymers include polyamide (for example nylon), polybenzimidazole (PBI), polyethylene (PE), polypropylene (PP), polystyrene (PS), polyvinyl chloride (PVC) and polytetrafluoroethylene (PTFE). Aptly, the liquid polymer comprises polystyrene, for example the liquid polymer comprises a polystyrene casting resin. A polystyrene casting resin may be cured with a curing agent, for example methyl-ethyl ketone peroxide catalyst.

In one embodiment, the liquid polymer is an elastomer. Aptly, the liquid polymer is silicone. Aptly, the liquid polymer is a biomedical grade silicone. Aptly, the liquid polymer is MDX4-4210 biomedical grade silicone. MDX4-4210 biomedical grade silicone is a biomedical grade elastomer (as known as SILASTIC® MDX4-4210). Silicone is commercially available, for example SILASTIC® MDX4-4210 is commercially available from Dow Corning.

Silicone, for example MDX4-4210 silicone may be cured at room temperature. Alternatively, curing may be accelerated with heat. For example a temperature of 55° C. may result in a curing time of 2 hours. For example, a temperature of 75° C. may result in a curing time of minutes.

A process for the manufacture of a monolithic body may also comprise a step for the preparation of the liquid polymer for injection into the mould. Aptly, the liquid polymer may be prepared by mixing a curing agent with a base polymer. Aptly, the curing agent and base polymer mixture may be exposed to a full or partial vacuum, for example a vacuum of about 710 mm Hg for 10 to 50 minutes, e.g. approximately 30 minutes.

In one embodiment the mould comprises metal.
In one embodiment, the mould comprises one or more holes to release air that may be trapped inside the liquid polymer.
In one embodiment, the mould comprises plastic.
In one embodiment, the mould is prepared by machining e.g. drilling or milling. For example, the mould may be prepared by CNC (Computer Numerical Control) machining.

A monolithic module may comprise a monolithic body, a layer of first polymer and a layer of second polymer. In one embodiment, a monolithic body is substantially surrounded by a layer of first polymer and the layer of first polymer is substantially or partially surrounded by a layer of second polymer. The monolithic body may be described as having a double coating. The monolithic module may be provided with and inlet and/or outlet.

For example the first polymer is an elastomer, e.g. silicone. Aptly, the liquid polymer is a biomedical grade silicone. Aptly, the liquid polymer is MDX4-4210 biomedical grade silicone. MDX4-4210 biomedical grade silicone is a biomedical grade elastomer (as known as SILASTIC® MDX4-4210). Silicone is commercially available, for example SILASTIC® MDX4-4210 is commercially available from Dow Corning.

For example the second polymer is a plastic, for example the second polymer is selected from polycarbonate (PC), polymethylacrylate (PMMA), cyclic olefin copolymer (COC) and polyethylene (PE).

A process for the manufacture of a monolithic body having a double coating may comprise the steps of:
i) supplying a mould for injection moulding containing an inorganic monolithic body;
ii) injecting a liquid polymer (e.g. silicone as described herein) into the mould wherein the liquid polymer flows between a surface of the mould and a surface of the monolithic body and surrounds the monolithic body, except for the area of contact between the mould and monolithic body;
iii) setting the polymer to form a monolithic module;
iv) optionally, where necessary annealing the monolithic module;

The mould of step i) forms part of the monolithic module. There is thus formed a monolithic body comprising a double coated monolithic body.

In step i) the mould may be in the form of a plastic holder for example prepared by machining e.g. CNC (computer numerical control) machining. Alternatively the mould may be itself prepared by an injection moulding process, for example comprising a polymer selected from polycarbonate (PC), polymethylacrylate (PMMA), cyclic olefin copolymer (COC) and polyethylene (PE). Thus the process may further comprise (prior to step i)) the step of preparing a mould by machining or preparing a mould by injection moulding for example using a polymer selected from polycarbonate (PC), polymethylacrylate (PMMA), cyclic olefin copolymer (COC) and polyethylene (PE).

Another process for the manufacture of a monolithic body having a double coating may comprise the steps of:
i) supplying a mould for injection moulding containing an inorganic monolithic body;
ii) injecting a first polymer (e.g. silicone as described herein) into the mould to substantially surround a surface of the monolithic body;
iii) setting the polymer to form a partial monolithic module;

iv) inserting the partial monolithic module into a second mould for injection moulding;
v) injecting a second polymer (e.g. a plastic for example selected from polycarbonate (PC), polymethylacrylate (PMMA), cyclic olefin copolymer (COC) and polyethylene (PE)) into the mould to substantially surround a surface of the first polymer;
vi) setting the second polymer.

There is thus formed a monolithic body comprising a double coated monolithic body.

The process for the manufacture of a monolithic module may further comprise the step of providing the double coated monolithic module with an inlet and outlet. The inlet and outlet extend between the surface of the monolithic body and the outer surface of the monolithic module. The inlet and/or outlet may be provided by machining the monolithic module, for example by drilling or milling. The monolithic module may be machined after setting the polymer(s) and, if present, before or after the annealing step. In one embodiment, the inlet and/or outlet may be provided during the injection step(s) by using a mould adapted to provide an inlet and/or outlet.

DETAILED DESCRIPTION OF EMBODIMENTS OF THE INVENTION

Brief Description of the Drawings

Certain embodiments of the present invention will now be described herein, by way of example only, with reference to the accompanying non-limiting examples and drawings in which:

FIG. 8A is an image of a monolithic module according to certain embodiments of the present invention. The monolith is encased in silicone within a mould. As shown in FIG. 8, the monolith is located in a mould and comprises tubing leading to and exiting the monolith.

FIGS. 8B and 8C illustrate a cross section of three embodiments of a monolithic body having a double coating.

In the Figures, like reference numerals refer to like parts.

In order to incorporate an inorganic monolithic body into a microfluidic flow system for the separation of an analyte from a radioactive sample, the inventors have developed a process for preparing a monolithic module. Previously, a monolithic body could be prepared by a sol-gel process directly within a microfluidic channel or by heat shrink wrapping in PTFE for insertion into a microfluidic channel. However monolithic bodies prepared using prior art processes are often inconsistent in size and/or shape. The process developed by the inventors yields a monolithic module that can be easily and conveniently incorporated into a microfluidic flow system. The process is advantageous because the resulting monolithic modules and monolithic bodies contained therein have a consistent size and shape. The monolithic bodies prepared in this way are of a consistent size and shape and are hermetically sealed (except for the inlet and outlet) thus ensuring that the sample passes through the pores of the monolithic body and not along its outer interface of the monolithic body.

Figure 3:
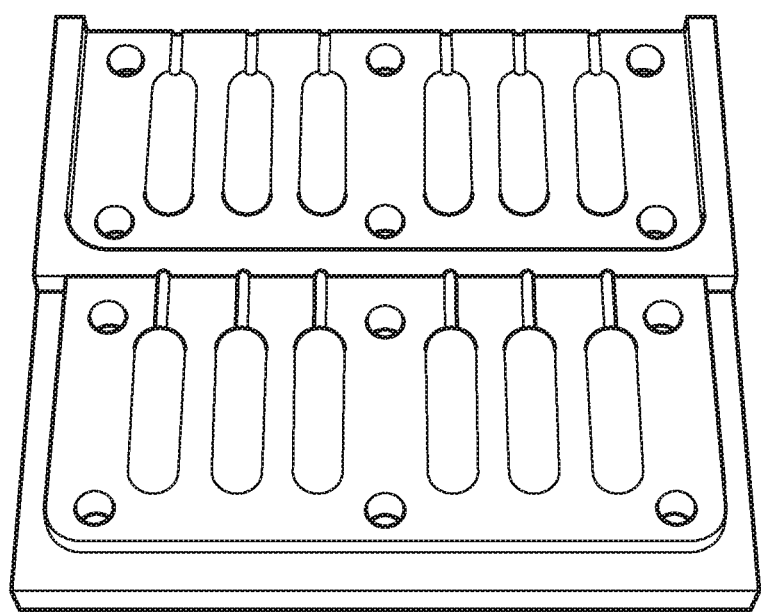
FIG. 3 illustrates a mould for the preparation of a monolithic body.

A monolithic body may be prepared for example as described herein (see example 1) using a mould as illustrated in FIG. 3. The monolithic body may be functionalised as appropriate according to its intended use. Methods for monolith functionalisation are known in the art, examples of which are described herein (see example 2).

Example 1: Preparation of Monolithic Body

A mould was designed using SolidWorks software which was also used to program the CNC machine. The CNC machine was then used to mill the mould out of PTFE. 0.282 g polyethylene oxide (PEO) was added to a 50 mL falcon tube and cooled with ice. 2.58 mL nitric acid (1 N) was added and the mixture stirred. 0.29 mL water was then added and the mixture left for 1 hour maintaining cooling. After 1 hour, 2.26 mL tetraethyl orthosilicate (TEOS) was added and stirring and cooling continued.

The PTFE mould (see, for example, as illustrated in FIG. 3) in two halves was put together in a holder and heated at 40° C. for 1 hour, after which the holder was tightened to ensure no leakage. After 1 hour of stirring, the PEO/TEOS mixture was injected into the mould ensuring the mould was filled and all air escaped. A clamp with a parafilm layer was placed against the mould inlets and tightened to seal the mould, and the whole apparatus heated to 40° C. for 72 hours. After this time, the clamp was removed and the two halves of the mould carefully separated.

The monolithic body formed in the mould was removed from the mould, rinsed with water and then soaked in water for 24 hours with regular replacement of the water to ensure the monolithic body was well washed.

The silica-based monolith shows nanopore diameter of 16 nm, nanopore volume 0.7 $cm^3/g$, and specific surface area 209 $m^2/g$.

The monolithic body was added to a mixture of 40 ml water and 10 ml ammonium hydroxide (5 M) and the mixture heated for 16 hours at 90° C. under reflux. After this time, the monolithic body was removed from the mixture and placed in water. The water was replaced regularly for the next 8 hours, after which the monolithic body was dried at 40° C. Finally the monolithic body was heated to 550° C. in a furnace for 3 hours. When cool the monolithic body was ready for use.

For further details on the preparation of silica monoliths please see P. D. I. Fletcher, S. J. Haswell, P. He, S. M. Kelly, A. Mansfield, J Porous Mater. 2011, 18, 501.

Example 2: Functionalization of Monolithic Body 2.a. Preparation of Cation-Exchange Monolithic Body The desired amount of 3-mercaptopropyltrimethoxysilane is added to a solution containing 10 mL ethanol and 10 mL water, followed by the addition of a silica monolith. The mixture is refluxed overnight. The monolith comprising thiol surface groups is recovered and washed with water to remove unreacted reagents. The obtained silica monolith is oxidized by reaction with 10 mL hydrogen peroxide (30%) in 10 mL water and 10 mL methanol overnight at 60° C. The monolith is recovered and washed with water, and treated with 10 mL of 1 M $H_2SO_4$. The sulfonic acid modified monolith is washed with water and dried at 60° C. overnight.

This cation-exchange monolith shows a CEC (cation exchange capacity) of 181 peq/g.

2.b. Preparation of Anion-Exchange Monolithic Body

The desired amount of silica monolith is added to anhydrous toluene. To this is added a solution containing 0.12 mL methyltrichlorosilane and 0.3 M 3-chloropropyltrichlorosilane in anhydrous toluene. The reaction is conducted at 80° C. under nitrogen atmosphere for 24 hours. After this, the monolith is recovered and washed with dichloromethane, methanol, water and methanol to remove unreacted reagents and then dried at 60° C. overnight. Following this, the monolith is treated with N,N-dimethylethanamine in DMF at 80° C. for 24 hours to form positively charged groups on the surface of the silica monolith.

2.c. Preparation of Reverse Phase Silica Monolith

The desired amount of silica monolith is added to a solution of 1.57 mmol octadecyltrimethoxysilane in toluene. The reaction is conducted at 80° C. overnight. The monolith is recovered and washed with toluene and dried at 60° C. overnight.

For further details on the functionalization of silica monoliths please see C. S. Gill, B. A. Price, C. W. Jones, J Catal. 2007, 251, 145 or C. R. Silva, C. Airoldi, K. E. Collins, C. H. Collins, LCGL North America 2004, 22, 632.

Example 3: Synthesis of Silicon Nitride, Silicon Imido Nitride and Silicon Silicon Imide Monolithic Bodies Details for the preparation of certain silicon nitride materials can be found in WO 2006/046012 which describes a sol-gel procedure for the preparation of materials based on silicon nitride and silicon oxynitride. Monolithic bodies comprising silicon imido nitride, silicon imide and/or silicon nitride and processes for their preparation are disclosed in WO 2013/054129. Monolithic bodies comprising silicon imido nitride, silicon imide and/or silicon nitride as described herein can be prepared according to the preparation procedures described in WO 2006/046012 and WO 2013/054129.

Silicon diimide mesoporous gel is optionally partially pyrolysed to form a silicon imido nitride, or completely pyrolysed to form a silicon nitride ceramic material.

Figure 1:
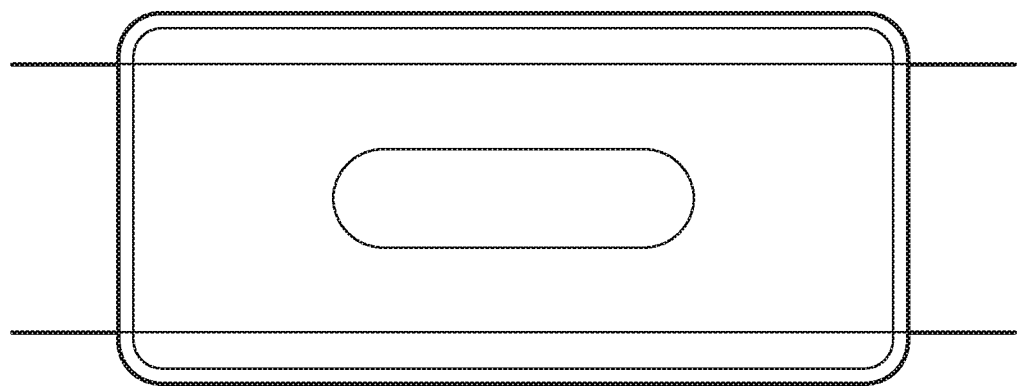
FIG. 1 is an image of a monolithic body made according to certain embodiments of the present invention.
Figure 2:
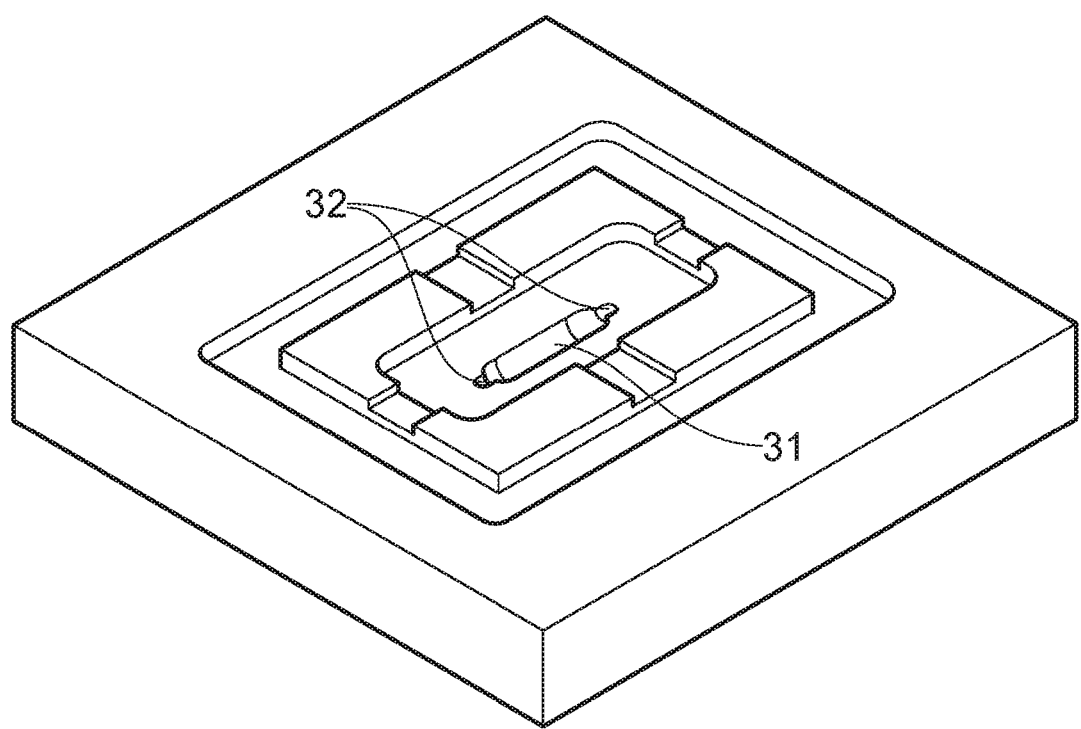
FIG. 2 illustrates a mould for injection moulding for the preparation of a monolith module.

Example 4: Preparation of Monolithic Module 4.1 Preparation of Monolithic Module Using a Two Mould Process Once functionalised, the monolithic body must be hermetically sealed to ensure that, when administered, fluid flows through the monolithic body and not around the monolithic body, for example at the interface between the monolithic body and housing. This can be achieved by forming a monolithic module according to an aspect of the invention. In particular, the monolithic body may be placed in the first of two moulds as shown in FIG. 2 with half of the monolithic body held in a recess (31). The monolithic body is secured in place by a protrusion (32) at each end of the monolithic body which extends to the centre of the primary axis of the monolithic body and remains in contact during a first moulding step. Molten polymer is injected into the first mould and allowed to set forming a first module part over the monolithic body. This resulting first module part with integrated monolithic body is placed in a second mould with the module surface opposite the monolithic body and module sides held within a recess. Molten polymer is injected into this second mould over the exposed monolithic body surface and bonds to the surface of the first module part. After setting, the complete monolithic module is annealed in a furnace. Inlet and outlet holes (41) can be moulded into the monolithic unit during the moulding process or may be machined into the monolithic module. A monolithic module prepared by this process (FIG. 4) comprises a monolithic body (42) which is hermetically sealed except for the inlet and outlet (41).

4.2 Preparation of a Monolithic Module Comprising a Silicone Moulding

MDX4-4210 biomedical silicone was prepared by mixing 1 part of curing agent with 10 parts by weight of base elastomer. The mixture was then exposed to a vacuum of about 710 mm Hg for approximately 30 minutes to remove any trapped air from the silicone. A monolithic module was prepared by moulding MDX4-4210 biomedical silicone around a monolithic body. A monolithic body was placed in a mould and positioned such that there was a distance of at least 1 mm from the surface of the monolithic body to the surface of the mould. The mould was provided with air holes to release air trapped within the uncured silicone. The mould was also provided with holes for tubing which tubing held the monolithic body in place and allowed for adjustment of the monolithic body within the mould (see FIG. 8).

The silicone mixture was added to the mould to completely cover the monolith and also the tubing provided within the mould and cured at 55° C. for 2 hours.

The resulting module was found to comply with leakage and stability requirements at a flow rate of 1 ml/min. Chemical compatibility was observed with acetonitrile and sodium hydroxide. No volume change was observed following immersion of the module in acetonitrile for 20 hours at 24° C. Volume changes following immersion in sodium hydroxide were observed as follows:

+9% volume increase at 50% concentration for 7 days at 70° F.

−2% volume increase at 20% concentration for 7 days at 70° F.

+1.2% volume increase at 20% concentration for 3 days at 212° F.

Example 5: Use of Monolithic Body to Isolate $^{68}Ga$

A cation exchange monolith has been used to quantitatively trap and recover $^{68}Ga$ from a decay generator. Use of a commercial cation exchange resin has only recovered about 50% $^{68}Ga$.

An aqueous radioactive substance for example $^{68}Ga$ solution is passed through a cation-exchange monolith column so that the $^{68}Ga$ is trapped on the monolith. The monolith is then washed with organic based solution and the column eluted with a small volume of organic based solution to release at least 95% $^{68}Ga$.

By addition of the required reagent i.e. DOTA, NOTA or DTPA to the obtained $^{68}Ga$ solution, excellent labelling yield can be obtained, for example 99% for DOTA (20 μM DOTA, 95° C., 10-20 min), 99% for NOTA (100 μM NOTA, room temperature, 10 min), and 96% for DTPA (20 μM DTPA, 95° C., 20 min).

After labelling/or synthesis of radiotracer the reaction mixture then passes through a reverse phase (C18) monolithic column for purification.

Figure 7:
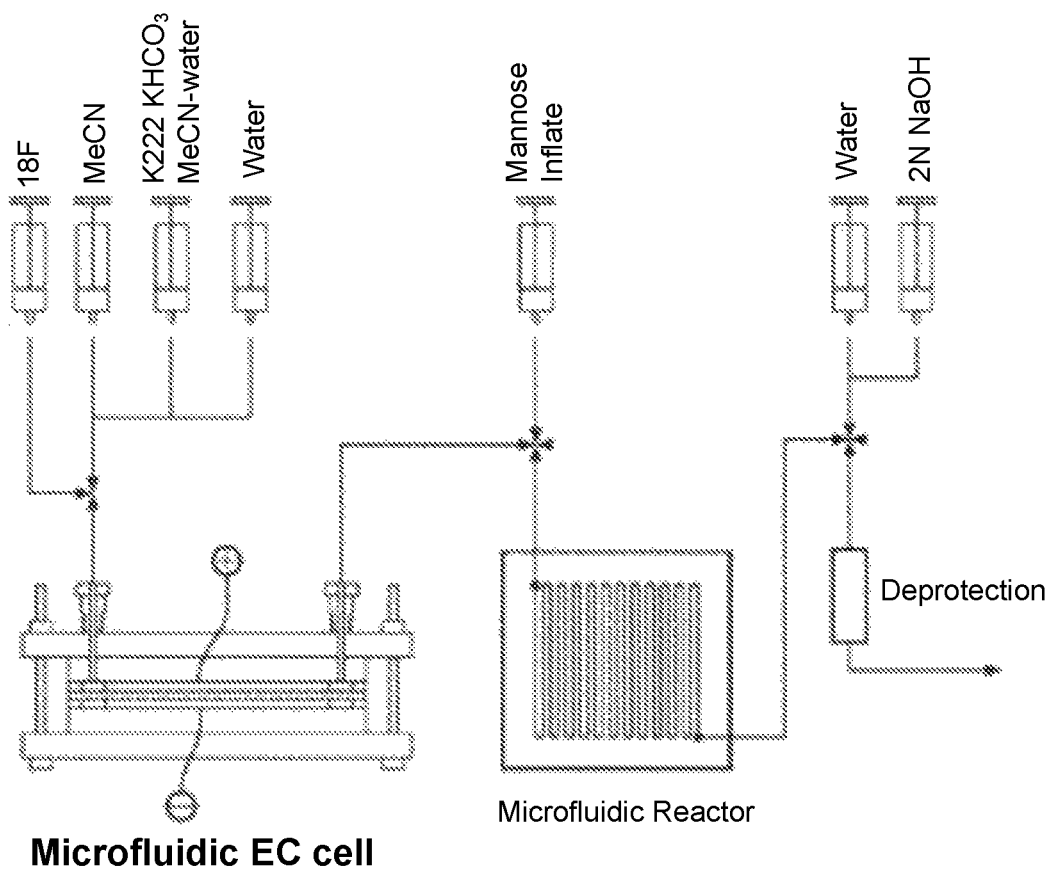
FIG. 7 is a schematic diagram of a microfluidic system. The monolith is indicated by "deprotection".

Example 6: Synthesis of Radiotracer [$^{18}$F]FDG 0.2-0.3 mL of an aqueous solution of $^{18}$F is passed through an electrode trapping cell at a flow rate of 0.2 mL/min under a constant electric potential (14-20 V) applied between carbon and Pt electrodes. The cell is then flushed with anhydrous MeCN (0.5 mL/min, 1 min) while the voltage is disconnected. 0.1 mL of organic based solution containing the K222 and KHCO$_3$ in MeCN—H$_2$O (1-10%) is passed through the cell at flow rate of 0.1 ml/min under a reversed potential (2-4 V) while the cell is heated to a preset temperature of 80° C. and the released solution is stored in a sample loop. The released solution containing $^{13}$F, K222 and KHCO$_3$ is pushed by MeCN at flow rate of 0.02 ml/min to mix with 0.1 ml of mannose triflate solution (0.02 mL/min) inside a Y-micromixer then together entering a microreactor (volume 0.05 mL) heated at 100° C. The reaction solution is mixed with a flow of H$_2$O (0.04-0.12 mL/min) then passed through a C18-monolith column for trapping the labelled precursor. The monolith is washed with water and dried with N$_2$. A 0.4 ml of 2 N NaOH solution is loaded into the monolith and hydrolysis is maintained at room temperature for 2 min and the product [$^{18}$F]FDG is eluted out with 1-5 mL of water, which is passed through cation-, anion-, silica- and C18-monoliths for purification of [$^{18}$F]FDG. This process is shown schematically in FIG. 7.

Figure 5:
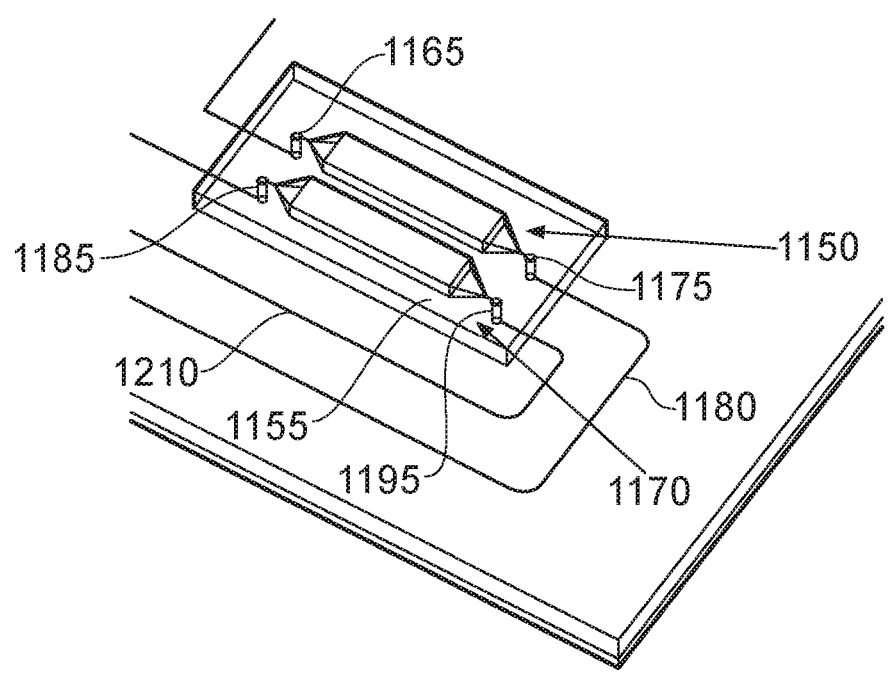
FIG. 5 illustrates part of a microfluidic flow system comprising a monolithic module.
Figure 6A:
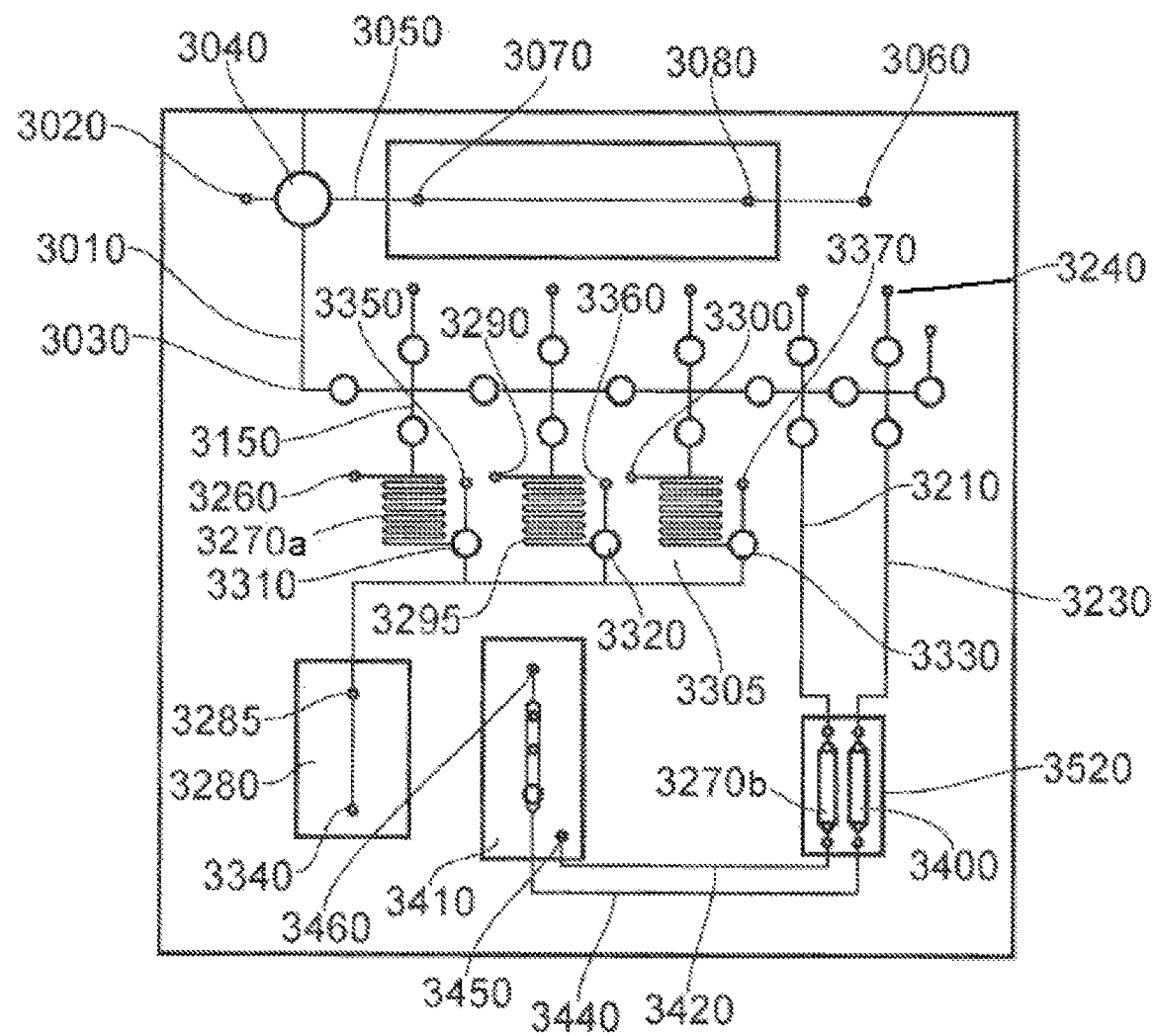
FIGS. 6A and 6B illustrates a microfluidic chip for quality control comprising a monolithic module.
Figure 6B:
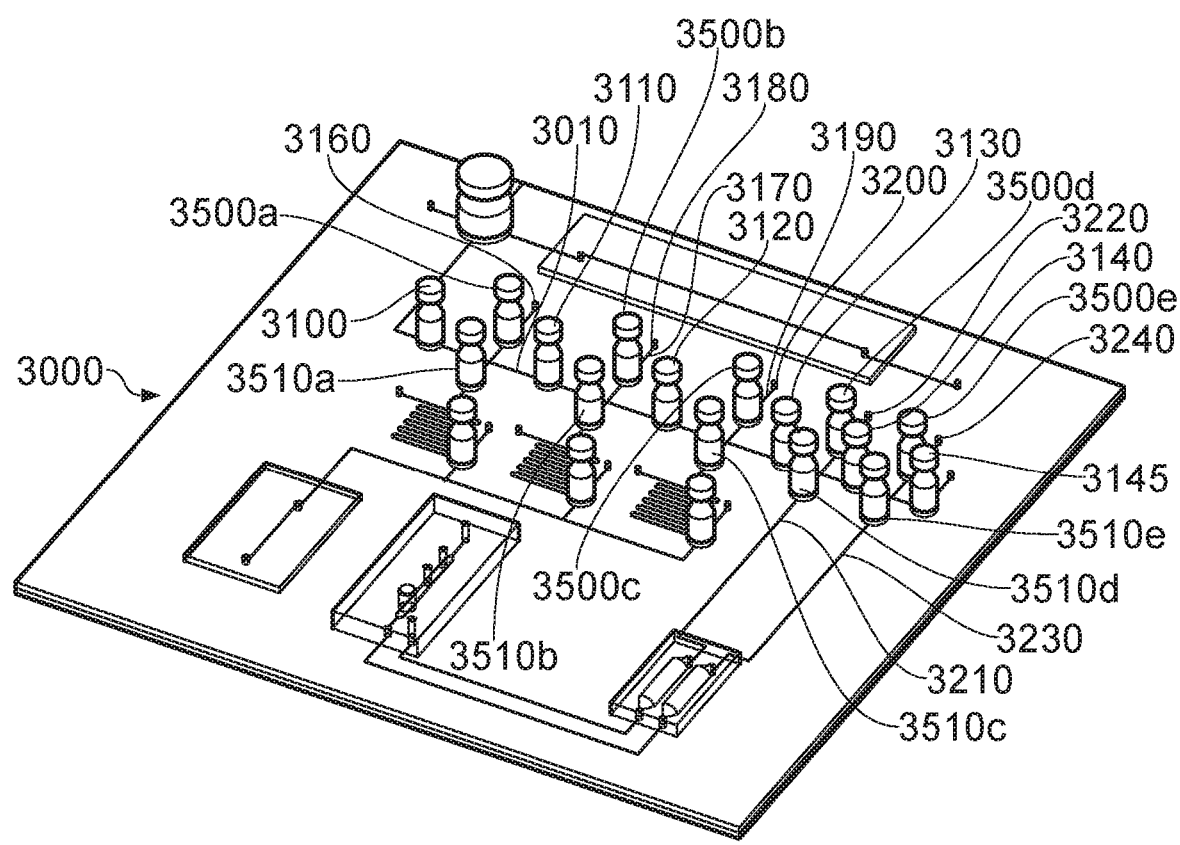

As described herein, a monolithic body and/or a monolithic module (FIG. 4) may be incorporated into a microfluidic flow system (FIG. 5), for example into a microfluidic chip for quality control (FIG. 6). Quality control analysis of a sample may be required prior to administration to a patient.

Figure 4:
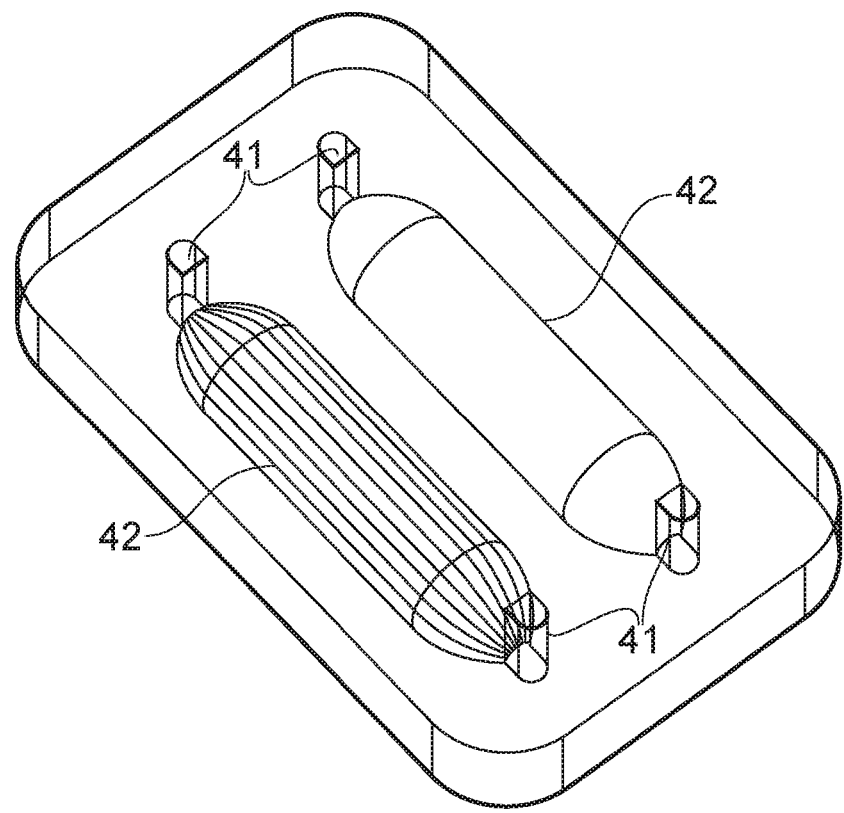
FIG. 4 illustrates a monolithic module comprising 2 monolithic bodies.

FIG. 4 illustrates a monolithic module comprising a first monolithic body and a second monolithic body which may be incorporated into the chips of certain embodiments described herein. The monolithic module may be injection moulded.

FIG. 5 illustrates how a microfluidic module may be incorporated into a microfluidic chip. The first intersecting channel is connected to an upstream portion of the first separation element 1150 such that fluid, e.g. the sample, in the first intersecting channel can flow through the first separation element. In the exemplified embodiment, the first separation element is a strong anionic exchange (SAX) monolithic liquid chromatography column. In one embodiment, the first reaction zone is comprised in a modular component 1155 which is secured to the upper surface of the upper planar structure such that the first intersecting channel is in fluid communication with the first separation element. Thus, the modular component comprises an inlet 1165 and a flow channel which are in fluid communication with the first intersection channel and the first separation element. Similarly, the modular component comprises an outlet 1175 downstream from the first separation element which is in fluid communication with the channel 1180 in use to allow the sample to flow from the first separation element to the channel 1180. The first separation element comprises a monolithic body.

A second intersecting channel is in fluid communication with a second separation element 1170. The second separation element comprises a monolithic body which may a silica monolith or a C18-modified silica monolith. The second separation element 1170 is connected at a downstream end region thereof to a further microchannel 1210 which is in turn fluidly connected to an outlet (not shown). The module may comprise an inlet port 1185 which is in fluid communication with the second separation element. The module may also comprise an outlet port 1195 which is in fluid communication with a microchannel 1210.

An embodiment of a chip and system is shown in FIG. 6. The microfluidic chip (3000) includes a first microchannel 3010 which is in fluid communication with an inlet port 3020. A sample fluid can be introduced into the microfluidic chip through the inlet port 3020.

The first microchannel 3010 comprises a first valve element 3040 which can control movement of a fluid e.g. the sample into the first microchannel.

The chip illustrated in FIG. 6 comprises an additional microchannel 3050, referred to as a sample channel. The sample channel is in fluid communication with the sample inlet port 3020. The sample channel intersects the first microchannel. The first valve element may be a multidirectional valve which controls movement of the sample either to the sample channel or the first microchannel depending on the requirement of the user.

The sample channel is in fluid communication with an outlet 3060. Aptly, the sample channel is not connected to any further inlets. As such, no reagents are added to the sample in the sample channel and the sample may be suitable for administration to a patient in need thereof. Whether the sample is administered will be dependent on the outcome of the one or more tests carried out by the system of embodiments of the present invention and determination of the characteristics of the sample.

The sample channel may be in fluid communication with one or more detection channels as described herein. A first detection channel 3070 is provided which can be used to determine a characteristic such as for example clarity and/or appearance of the sample.

A second detection channel 3080 may be provided downstream from the first detection channel.

The first detection channel and the second detection channel may be in fluid communication via a portion of the sample channel which is provided in the lower planar structure. Thus, in use, a sample is flowed along the sample channel, down the first detection channel, along the sample channel in the lower planar structure and then upwardly along the second detection channel. The sample then exits via the outlet 3060.

Aptly, the first microchannel comprises a plurality of valve elements which can be used to direct flow of the sample and/or reagents and/or solutions from the first microchannel to other areas of the microfluidic chip. In addition the valve elements can be used to isolate portions of a fluid in the first microchannel from other areas of the first microchannel. Aptly, the valve elements are provided in series.

Thus, the first microchannel 3010 may comprise a second valve element 3100, a third valve element 3110, a fourth valve element 3120, a fifth valve element 3130, a sixth valve element 3140 and a seventh valve element 3145. Ultimately, the number of valve elements may depend on how many tests are to be provided on the chip and thus how many detection zones portions of the sample are to be directed to.

The first microchannel may comprise an approximately 90 degree change in direction (3030) between the first valve element and the second valve element.

A first intersecting channel 3150 may be provided on the chip. The first intersecting channel 3150 is in fluid communication with a further inlet, referred to herein as the second inlet port 3160. The first intersecting channel intersects the first microchannel at a junction between the second valve element 3100 and the third valve element 3110.

As described herein, each intersecting channel may be provided with a pair of valve elements which prevent flow of fluid from the detection zones during filling of the first microchannel with the sample. Aptly, one of the pair of valve elements is provided in the intersecting channel upstream of the junction between the intersecting channel and one of the pair is provided downstream from the junction. The valve elements, indicated by 3500a, 3500b, 3500c, 3500d, 3500e and 3510a, 3510b, 3510c, 3510d and 3510e are placed in a closed position when the first microchannel is filled with the sample. Once flow of the sample or portion thereof to a detection zone is desired, the valves of the intersecting channel can be opened to provide a fluid flow path to the detection zone.

Downstream from the junction, the first intersecting channel is in fluid communication with a reagent inlet port 3260. Further downstream from the reagent inlet port 3260, the first intersecting channel comprises a serpentine mixing portion 3270a. The first intersecting channel is in fluid communication with a detection zone 3280. The detection zone aptly comprises a third detection channel 3285 which extends at least partially through the thickness of the chip and provides a pathlength between a source and a detector.

A second intersecting channel 3170 is provided on the chip. The second intersecting channel is in fluid communication with an inlet port 3180, referred to as a third inlet port. The second intersecting channel intersects the first microchannel 3010 at a junction between the third valve element 3110 and the fourth valve element 3120. In the illustrated embodiment, the second intersecting channel has a similar structure to the first intersecting channel. The second intersecting channel is in fluid communication with a second reagent inlet port 3290 at a position downstream from the junction. The second intersecting channel comprises a serpentine mixing zone 3295 in which a portion of the sample and a reagent introduced via the second reagent inlet port can be mixed together prior to entering the detection zone.

The chip may also comprise a third intersecting channel 3190. The third intersecting channel is in fluid communication with an inlet port 3200, referred to as a fourth inlet port. The third intersecting channel intersects the first microchannel at a junction between the fourth valve element 3120 and the fifth valve element 3130. The third intersecting channel is in fluid communication with a third reagent inlet port 3300 at a position downstream from the junction. The second intersecting channel comprises a serpentine mixing zone 3305 in which a portion of the sample and a reagent introduced via the second reagent inlet port can be mixed together prior to entering the detection zone.

One or more valve elements 3310, 3320, 3330 may be provided to control flow of a fluid in the first, second and/or third intersecting channels to the detection zone. Thus, the valve elements can be used to selectively move fluid e.g. a mixture of a portion of the sample and a reagent from one but not the other intersecting channels. Thus, only one mixture of sample and reagent is directed to the detection zone and into the detection channel at a time.

The microfluidic chip may additionally comprise one or more inlet ports for introducing a solution e.g. a washing solution or a standard solution through the detection zone. These inlet ports 3350, 3360 and 3370 are aptly provided upstream to the valve elements thus enabling flow of a fluid introduced through these inlet ports to the detection zone be controlled.

The detection zone may comprise an outlet 3340 for removing fluid which has travelled along the detection channel.

In alternative embodiments, each of the first, second and third intersecting channels may be in fluid communication with a detection channel. That is to say in place of the third detection channel depicted in FIG. 6, a plurality of detection channels, each connected to a single intersecting channel, may be provided. In such embodiments, determination of a plurality of characteristics using the detection channels may take place simultaneously.

The chip may also comprise a fourth intersecting channel 3210 which intersects the first microchannel at a junction between the fifth 3130 and sixth valve elements 3140. The fourth intersecting channel 3210 is aptly in fluid communication with an inlet port 3220, referred to as a fifth inlet port, provided upstream from the junction. The fourth intersecting channel is in fluid communication with a further detection zone 3520 which comprises a second separation element 3270b. The second separation element is a monolithic body. The second separation element is as described above. The second separation element may be comprised in a separate module which is provided on the upper surface of the upper planar surface in use. The separation module is a monolithic module. The second separation element is in fluid communication with a microchannel 3420 which flows to a detection zone which also comprises an electrochemical cell 3410. The electrochemical cell is as described above. The second separation element is in fluid communication with an outlet 3450 provided in the electrochemical cell.

The chip also comprises a fifth intersecting channel 3230 which intersects the first microchannel at a junction between the sixth valve element 3140 and the seventh valve element 3145. An inlet port 3240 referred to as a sixth inlet port, is provided in fluid communication with the fifth intersecting channel upstream from the junction.

The fifth intersecting channel 3230 is in flow communication with a first separation element 3400 provided in the further detection zone 3520. The first separation element is a monolithic body. The first separation element is as described above.

The first separation element 3400 is in fluid communication with a further microchannel 3440 which flows into an electrochemical cell 3410. The electrochemical comprises a working electrode, a reference electrode and a counter electrode as described above. The chip may further comprise an outlet 3460 downstream from the electrodes of the electrochemical cell.

Figure 9A:
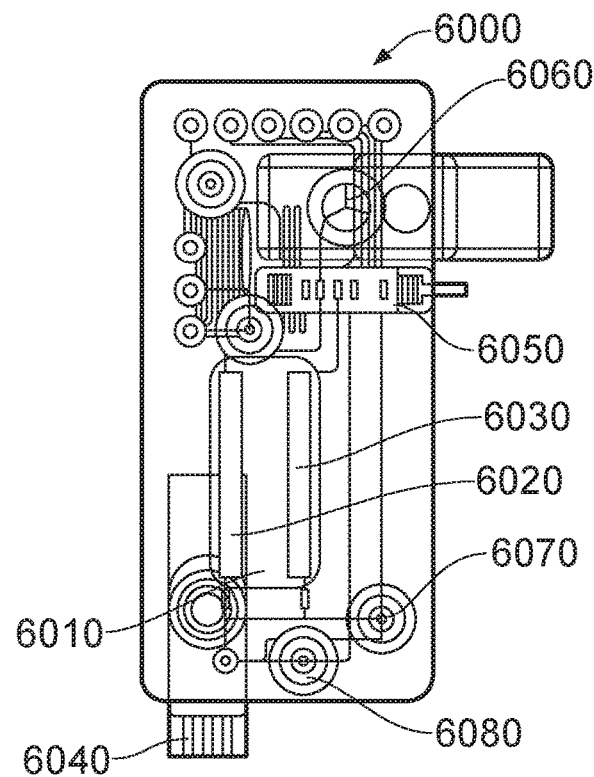
FIGS. 9A and 9B illustrates a microfluidic chip for quality control comprising a monolithic body according certain embodiments.
Figure 9B:
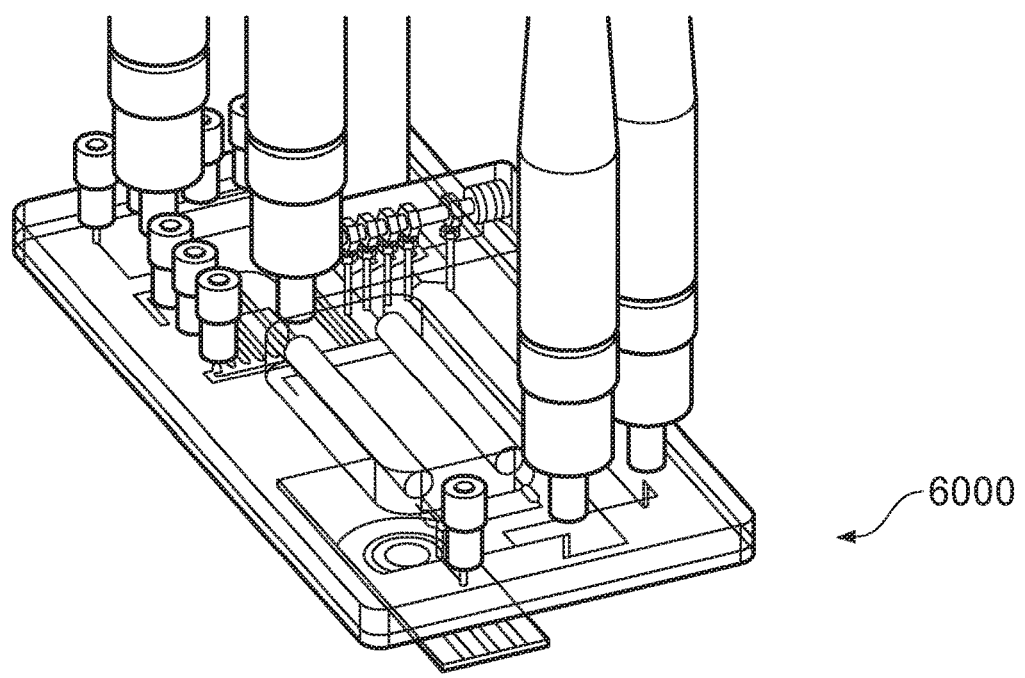

FIG. 9 illustrates a chip 6000 according to certain embodiments of the invention. The chip comprises a separable component 6010 which comprises two monolithic bodies 6020 and 6030 as described herein. The chip also incorporates an electrochemical cell 6040 which in the illustrated embodiment is a screen printed electrode. The electrode may be slid into a recess in the chip.

The chip also comprises a Raman chamber 6060. A pin valve membrane 6050 is provided to control flow of a sample to the Raman chamber. The chip comprises a plurality of inlets and outlets as described herein. Furthermore, the chip is provided with a plurality of detection channels. Fibres, for example, the fibres 6070 and 6080 are positioned adjacent to an end of a respective detection channel for spectroscopic analysis of a solution, e.g. a portion of a sample, which is provided in the detection channel.

In another embodiment, a microfluidic based system (FIG. 7) has been developed for [$^{18}$F]FDG synthesis in which a microfluidic electrochemical cell is used for the separation of [$^{18}$F]fluoride from [$^{18}$O]water, a serpentine channel microreactor for the radiolabeling reaction and C18-column for performing hydrolysis of trapped ACY-FDG. The C18-column may be a reverse phase monolithic body comprised in a monolithic module. This system is advantageous because it eliminates evaporation steps for solvent-exchange in both processes of labeling reaction and hydrolysis reaction. The elimination of evaporation process offers an opportunity to realize dose-on-demand production in an integrated system. Under optimal parameters [$^{18}$F] fluoride activity of 94-99% (initial activity up to 30 mCi) can be efficiently trapped within 1-2 min and over 96% of trapped [$^{18}$F]fluoride can be released into either MeCN-water (4%) or DMF-water (4%) containing K222-KHCO$_3$ within 5-6 min. Using this released solution for fluorination of mannose triflate, 100% ACY-FDG can be obtained within 1.2 min at 100° C. After basic hydrolysis (2 min) at room temperature 98.3% FDG can be achieved without further purification.

The first embodiment of FIG. 8 b) illustrates a cross section of a double coated monolithic body where the outer coating is made up of the plastic holder or mould into which silicone was poured and subsequently moulded around the monolithic body.

The second embodiment of FIG. 8 c) illustrates a double coated monolithic body where the outer coating is made itself by injection moulding. The outer coating may first be prepared by injection moulding and the silicone subsequently injected into it around the monolithic body. Alternatively the silicone coating is applied first by injection moulding and the outer layer subsequently applied by injection moulding. The outer coating may have various cross section shapes as shown.

The invention claimed is:

1. A process for separating an analyte from a radioactive sample, comprising:
    eluting the radioactive sample comprising the analyte through a chromatographic monolithic body, wherein:
    the chromatographic monolithic body is hermetically sealed within a polymer housing;
    the polymer housing comprises an inlet and an outlet and is prepared by molding a polymer around the chromatographic monolithic body;
    the chromatographic monolithic body, inside of the housing, is incorporated onto a surface of a microfluidic chip;
    the chromatographic monolithic body is selected from an inorganic monolithic body comprising functionalized silica and a normal phase monolithic body; and
    the microfluidic chip is part of a microfluidic flow system.

2. The process according to claim 1 wherein the inorganic monolithic body comprising functionalized silica is selected from: a cation exchange monolithic body; an anion exchange monolithic body; and a reverse phase monolithic body.

3. The process according to claim 1 wherein the inorganic monolithic body has a length of from 10 mm to 80 mm and a diameter of from 3 mm-5 mm.

4. The process according to claim 1 wherein the inorganic monolithic body has a length of from 10 mm to 80 mm and a width of from 2 mm-6 mm.

5. The process according to claim 1 wherein the radioactive sample is added to the inorganic monolithic body in a volume of 10 nl-100 ml.

6. A process for preparing a radiopharmaceutical, comprising:
    i) concentrating a radioisotope;
    ii) synthesizing the radiopharmaceutical;
    iii) purifying the radiopharmaceutical; and
    iv) analyzing the radiopharmaceutical;
    wherein at least one of steps i), ii) iii), and iv) comprises a process according to claim 1.

7. The process according to claim 6 wherein step i) is a process according to claim 1, the analyte is a radioisotope selected from [$^{18}$F]fluoride, and [$^{68}$Ga]gallium, or [$^{68}$Ga] cation, and the radioactive sample is a radioactive solution produced from a cyclotron or a decay generator.

8. The process according to claim 6 wherein step ii) is a process according to claim 1, the analyte is a radiopharmaceutical precursor or protected form thereof and the radioactive sample is a reaction mixture.

9. The process according to claim 6 wherein step iii) is a process according to claim 1 and the analyte is a radiopharmaceutical selected from $^{18}$F-FLT ([$^{18}$F]fluorothymidine), $^{18}$F-FDDNP (2-(1-{6-[(2-[$^{18}$F]fluoroethyl)(methyl)amino] 2-naphthyl}ethylidene)malonitrile), $^{18}$F-FHBG (9-[4-[$^{18}$F] fluoro-3-(hydroxymethyl)butyl]guanine or [$^{18}$F]penciclovir), $^{18}$F-FESP ([$^{18}$F]fluoroethylspiperone), $^{18}$F-p-MPPF (4-(2-methoxyphenyl)-1-[2-(N-2-pyridinyl)-p-[$^{18}$F] fluorobenzamido]ethylpiperazine), $^{18}$F-FDG (2-[$^{18}$F]fluoro-2-deoxy-D-glucose), $^{18}$F-FMISO ([$^{18}$F]fluoromisonidazole) and $^{18}$F-sodium fluoride.

10. The process according to claim 6 wherein step iii) is a process according to claim 6, the analyte is an impurity and the radioactive sample is a solution of radiopharmaceutical.

11. The process according to claim 10 wherein the impurity is selected from $^{18}$F and endotoxin, and the inorganic monolithic body is a normal phase monolithic body.

12. The process according to claim 10 wherein the impurity is selected from acetylated [$^{18}$F]FDG, acetylated [$^{18}$F] FDM (fluoro-2-deoxy-D-mannose), acetylated ClDG (2-chloro-2-deoxy-D-glucose), mannose triflate and K222 (Kryptofix 2.2.2), and the inorganic monolithic body is a reverse phase monolithic body.

13. The process according to claim 10 wherein the impurity is selected from K222 and sodium hydroxide, and the inorganic monolithic body is a cation exchange monolithic body.

14. The process according to claim 10 wherein the impurity is selected from hydrochloric acid and a complexed metal radioisotope, and the inorganic monolithic body is an anion exchange monolithic body.

15. The process according to claim 6, wherein: step iii) is a process according to claim 1; the analyte is selected from [$^{18}$F]fluoride, [$^{18}$F]acetylated-FDG and [$^{18}$F]FDG; and the inorganic monolithic body is selected from a reverse phase monolithic body and a normal phase monolithic body.

16. The process according to claim 6, wherein: step iii) is a process according to claim 1, and the analyte comprises [$^{18}$F]fluoride, [$^{18}$F]acetylated-FDG and [$^{18}$F]FDG which are separated from each other by the inorganic monolithic body.

17. The process according to claim 6, wherein: step iii) is a process according to claim 1, and the analyte comprises [$^{18}$F]FDG and [$^{18}$F]FDM which are separated from each other by the inorganic monolithic body.

18. The process according to claim 6 further comprising, after concentrating the radioisotope, activating the radioisotope.

19. The process according to claim 18, wherein the radioisotope is activated by solvent exchange.

20. The process according to claim 6, wherein the radiopharmaceutical is synthesized by labeling a non-radioactive analogue of the radiopharmaceutical with the radioisotope.

* * * * *